US012797348B2

(12) United States Patent
Khurana et al.

(10) Patent No.: US 12,797,348 B2
(45) Date of Patent: Nov. 17, 2026

(54) UTROPHIN UPREGULATION COMPOUNDS FOR DUCHENNE MUSCULAR DYSTROPHY THERAPY

(71) Applicants: THE TRUSTEES OF THE UNIVERSITY OF PENNSYLVANIA, Philadelphia, PA (US); University of Pittsburgh—Of the Commonwealth System of Higher Education, Pittsburgh, PA (US)

(72) Inventors: Tejvir S. Khurana, Narberth, PA (US); Donna M Huryn, Allentown, NJ (US)

(73) Assignees: The Trustees of the University of Pennsylvania, Philadelphia, PA (US); University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 1040 days.

(21) Appl. No.: 17/792,707

(22) PCT Filed: Jan. 14, 2021

(86) PCT No.: PCT/US2021/013517
§ 371 (c)(1),
(2) Date: Jul. 13, 2022

(87) PCT Pub. No.: WO2021/146483
PCT Pub. Date: Jul. 22, 2021

(65) Prior Publication Data

US 2023/0076977 A1 Mar. 9, 2023

Related U.S. Application Data

(60) Provisional application No. 62/961,191, filed on Jan. 14, 2020.

(51) Int. Cl.

| | |
|---|---|
| ***A61K 31/165*** | (2006.01) |
| ***A61K 31/18*** | (2006.01) |
| ***A61K 31/343*** | (2006.01) |
| ***A61K 31/4045*** | (2006.01) |
| ***A61K 31/4184*** | (2006.01) |
| ***A61K 31/423*** | (2006.01) |
| ***A61K 31/44*** | (2006.01) |
| ***A61K 31/519*** | (2006.01) |

(52) U.S. Cl.
CPC ............ *A61K 31/165* (2013.01); *A61K 31/18* (2013.01); *A61K 31/343* (2013.01); *A61K 31/4045* (2013.01); *A61K 31/4184* (2013.01); *A61K 31/423* (2013.01); *A61K 31/44* (2013.01); *A61K 31/519* (2013.01)

(58) Field of Classification Search
CPC .................................................... A61K 31/165
See application file for complete search history.

(56) References Cited

U.S. PATENT DOCUMENTS 8,264,642 B2 * 9/2012 Lee ..................... G02F 1/13718 349/86
2012/0010176 A1 1/2012 Khurana et al.

FOREIGN PATENT DOCUMENTS

WO WO-2009087238 A2 * 7/2009 .............. A61P 35/02

OTHER PUBLICATIONS

Moorwood et al., "A cell-based High-throughput screening assay for posttranscriptional utrophin upregulation", J Biomol Screen., Apr. 2013 (Year: 2013).*

"Technical Manual for Bright-Glo Luciferase Assay System", Promega, Revised Mar. 2024 (Year: 2024).*

"Muscular Dystrophy", NIH, Mar. 13, 2026 (Year: 2026).*

Gordon et al., "Resveratrol decreases inflammation and increases utrophin gene expression in the mdx mouse model of duchenne muscular dystrophy", Clinical Nutrition, Feb. 2013 (Year: 2013).*

Bogdanovich et al., "Functional improvement of dystrophic muscle by myostatin blockade." Nature 420.6914 (2002): 418-421.

Chakkalakal et al., "Modulation of utrophin A mRNA stability in fast versus slow muscles via an AU-rich element and calcineurin signaling." Nucleic acids research 36.3 (2008): 826-838.

Grounds et al., "Towards developing standard operating procedures for pre-clinical testing in the mdx mouse model of Duchenne muscular dystrophy." Neurobiology of disease 31.1 (2008): 1-19.

International Preliminary Report on Patentability from PCT/US2021/013517 dated Jul. 28, 2022.

International Search Report from PCT/US2021/013517 dated Jul. 12, 2021.

Krag et al., "Heregulin ameliorates the dystrophic phenotype in mdx mice." Proceedings of the National Academy of Sciences 101.38 (2004): 13856-13860.

Moens et al., "Increased susceptibility of EDL muscles from mdx mice to damage induced by contractions with stretch." Journal of Muscle Research & Cell Motility 14.4 (1993): 446-451. (Abstract).

Moorwood et al., "A cell-based high-throughput screening assay for posttranscriptional utrophin upregulation." Journal of Biomolecular Screening 18.4 (2013): 400-406.

Petrof et al., "Dystrophin protects the sarcolemma from stresses developed during muscle contraction." Proceedings of the National Academy of Sciences 90.8 (1993): 3710-3714.

Moorwood et al. "Drug Discovery for Duchenne Muscular Dystrophy via Utrophin Promoter Activation Screening", PLoS ONE. 2011. vol. 6(10), e26169, 11 pages, especially: p. 9, col. 2, para 6.

(Continued)

*Primary Examiner* — Andrew D Kosar
*Assistant Examiner* — Gillian A Hutter
(74) *Attorney, Agent, or Firm* — Mark S. Cohen; PEARL COHEN LLP

(57) ABSTRACT

The present invention provides methods for increasing expression of utrophin in a subject in need thereof, the method comprising administering to the subject a pharmaceutical composition comprising a post-transcriptionally utrophin upregulator compound. The present invention also provides methods for treating a subject having a muscular dystrophy. This invention further provides methods for high-throughput screening for a post-transcriptional utrophin upregulator compound.

18 Claims, 35 Drawing Sheets

(56) References Cited

OTHER PUBLICATIONS

Amirouche et al. "Converging pathways involving microRNA-206 and the RNA-binding protein KSRP control post-transcriptionally utrophin A expression in skeletal muscle", Nucleic Acids Research. 2014. vol. 42(6), pp. 3982-3997, especially: abstract; p. 3983, col. 1, para 2; p. 3983, col. 1, para 3; p. 3983, col. 2, para 5.

PubChem-CID-444732, Create Date: Jun. 1, 2005 (Jun. 1, 2005), p. 2, fig.

Loro et al. "High throughput identification of post-transcriptional utrophin upregulators for Duchenne muscle dystrophy (DMD) therapy", Scientific Reports. 2020. vol. 10:2132, 12 pages.

Tinsley et al., "Daily Treatment with SMTC1100, a Novel Small Molecule Utrophin Upregulator, Dramatically Reduces the Dystrophic Symptoms in the mdx Mouse", PloS one 6.5 (2011): e19189.

Tinsley et al., "Safety, tolerability, and pharmacokinetics of SMT C1100, a 2-arylbenzoxazole utrophin modulator, following single—and multiple—dose administration to healthy male adult volunteer." The Journal of Clinical Pharmacology 55.6 (2015): 698-707.

Markati et al., "Lessons Learned from Discontinued Clinical Developments in Ducheenne Muscular Dystrophy", Frontiers in Pharmacology 12 (2021): 735912.

* cited by examiner

| | Selleck ID | EC50 screen (μM) | EC50 count (μM) | Fold diff (a.u.) |
|---|---|---|---|---|
| 1 | S1045 | 0.013 | 1.591 | 119.815 |
| | S3020 | low | 0.012 | NA |
| | S1096 | low | 0.057 | NA |
| | S1030 | 0.013 | 0.117 | 9.210 |
| | S7648 | 0.012 | 0.064 | 5.406 |
| | S1095 | low | 0.160 | NA |
| 2 | S7652 | NA | NA | NA |
| 3 | S8043 | 2.438 | high | high |
| | S2779 | 3.218 | 8.169 | 2.538 |
| | S1194 | 1.991 | high | high |
| 4 | S1515 | 0.558 | high | high |
| | S1090 | 0.138 | 4.653 | 33.72 |
| | S7569 | 0.683 | high | high |
| | S2170 | 0.269 | 5.028 | 18.69 |
| | S1085 | 0.342 | high | high |
| | S2244 | 0.369 | 5.431 | 14.721 |
| 5 | S2759 | NA | 0.041 | NA |
| 6 | S2892 | NA | NA | NA |
| | S2349 | NA | 0.522 | NA |
| | S8376 | NA | NA | NA |
| | S3030 | NA | NA | NA |
| | S7917 | 0.034 | 0.236 | 6.972 |
| | S2422 | NA | 0.019 | NA |
| | S7665 | NA | NA | NA |
| | S7597 | 0.099 | high | high |
| | S7915 | 0.330 | 0.214 | 0.648 |
| | S7198 | 0.125 | 0.378 | 3.013 |

Screen Statistics

- # of compounds screened = 96,000
- # of hits selected (S:B > 1.7) for confirmation = 114
  - Z-score= 4 is ~1.5 fold increase in luciferase activity
  - Z-score=7 is ~2 fold increase in luciferase activity
- Hit Rate = ~0.1 %
- Average Z' = 0.75
- S:B window = 4-6

FIG. 10

| PID | Product Name | Smiles | Structures |
|---|---|---|---|
| cmp06 | 158662 | c1(n2c(ncc1)ncc2)c1cc(OC2C3CC(C2)CC3)c(cc1) OC |  |

| Luciferase Assay | Primary Assay | Counter Assay | |
|---|---|---|---|
|  |  |  | | y-axis: Z-scores
x-axis: Concentration (uM)

| PID | Product Name | Smiles | Structures |
|---|---|---|---|
| cmp48 | 279761 |  c1(C(=O)Nc2ccc(cc2)OC)c(nccc1)Cl | |

| Luciferase Assay | Primary Assay | Counter Assay | |
|---|---|---|---|
|  |  |  | | y-axis: Z-scores
x-axis: Concentration (uM)

| PID | Product Name | Smiles | Structures |
|---|---|---|---|
| cmp88 | 376498 | c1(c2ccc(cc2)NC(=O)c2c(cccc2)C)nc2c(o1)cccc2 |  |

| Luciferase Assay | Primary Assay | Counter Assay | |
|---|---|---|---|
|  |  |  | | y-axis: Z-scores
x-axis: Concentration (uM)

| PID | Product Name | Smiles | Structures |
|---|---|---|---|
| cmp100 | 399865 | c1(C(=O)NC(=S)Nc2ccc(cc2)N(C)C)cco1 |  | y-axis: Z-scores
x-axis: Concentration (uM)

| PID | Product Name | Smiles | Structures |
|---|---|---|---|
| cmp109 | 399251 | <br>c12c3c(ccc1C(=O)c1c(c2on3)cccc1)C(=O)NCC | |

| Luciferase Assay | Primary Assay | Counter Assay | |
|---|---|---|---|
|  |  |  | | y-axis: Z-scores
x-axis: Concentration (uM)

UTROPHIN UPREGULATION COMPOUNDS FOR DUCHENNE MUSCULAR DYSTROPHY THERAPY

GOVERNMENT INTEREST STATEMENT

This invention was made with government support under Grant Number NS-102838, awarded by the National Institute of Neurological Disorders and Stroke (NINDS)-National Institutes of Health. The government has certain rights in the invention.

FIELD OF THE INVENTION

This invention relates to methods for increasing expression of utrophin in a subject in need thereof, the method comprising administering to the subject a pharmaceutical composition comprising a post-transcriptionally utrophin upregulator compound. This invention also relates to methods for treating a subject having a muscular dystrophy and for treating and preventing muscle wasting caused by a lack or reduced expression of dystrophin protein in a subject. This invention further relates to methods for high-throughput screening for a post-transcriptional utrophin upregulator compounds.

BACKGROUND OF THE INVENTION

Duchenne muscle dystrophy (DMD) is a devastating X-linked neuromuscular disorder that effects approximately 1 in 3500 live males worldwide. DMD is caused by mutations in the DMD gene (dystrophin gene) resulting in the loss or severe reduction of dystrophin protein expression. Dystrophin is thought to provide structural support to muscle fibers by linking the sub-sarcolemmal actin cytoskeleton to the extracellular matrix via the dystrophin-associated glycoprotein complex. In the absence of dystrophin, the complex is lost from the sarcolemma and the myofiber becomes susceptible to damage during contraction-relaxation cycles. Increased damage leads to chronic inflammation and progressive replacement of contractile units with fibro-fatty tissue, contributing to significant muscle wasting. DMD patients are typically diagnosed in early childhood and become increasingly wheelchair dependent in their teens, with cardiac and respiratory failure being the major causes of morbidity and mortality. There is currently no definitive cure for the disease.

Corticosteroids, such as prednisone, have been in use for over 50 years for DMD and, while not specific as a therapeutic for DMD, can slow disease progression. Indeed, with early intervention, they have been shown to increase life span of patients. However, their use is associated with extensive side effects and toxicities exemplified by immune suppression, osteoporosis, and weight gain. Newer steroid drugs such as vamorolone and deflazacort are promising candidates that are suggested to retain beneficial effects of prednisone without many of the side effects. DMD-specific approaches, including viral gene therapy which aims to reintroduce shorter functional versions of the dystrophin gene, or exon skipping which utilizes stable oligonucleotides to skip of one or more exons in order to regain expression of shorter functional dystrophin, are currently in various stages of clinical evaluation. Because the resulting version of dystrophin transcript will be shorter than normal, however, these therapies would be predicted only to decrease the severity of the disease, i.e., convert from DMD to a milder Becker allelic form. Other approaches currently under development include promoting read-through of premature stop codons and correcting mutations using gene editing. However, these approaches are mutation-specific, and therefore, would be applicable to restricted subsets of DMD patients. In light of these inadequacies, there is a critical need for improved compositions and therapeutically effective methods for treating muscular dystrophies, including DMD and Becker muscular dystrophy, that are not mutation-specific methods.

SUMMARY OF THE INVENTION

In one aspect, this invention provides a method for increasing expression of utrophin in a subject in need thereof, the method comprising administering to the subject a pharmaceutical composition comprising a post-transcriptionally utrophin upregulator compound.

In another aspect, this invention provides a method for improving a dystrophic phenotype in a muscle of a subject having loss or reduction of dystrophin protein expression, the method comprising administering to the subject a pharmaceutical composition comprising a post-transcriptionally utrophin upregulator compound.

In an aspect, this invention provides a method for treating and preventing muscle wasting caused by a lack or reduced expression of dystrophin protein in a subject, the method comprising administering to the subject a pharmaceutical composition comprising a post-transcriptionally utrophin upregulator compound.

In another aspect, this invention provides a method for treating a subject having a muscular dystrophy, the method comprising administering to the subject a pharmaceutical composition comprising a post-transcriptionally utrophin upregulator compound.

In one aspect, this invention provides a method for high-throughput screening for a post-transcriptional utrophin upregulator compounds, the method comprising:

a) screening a plurality of compounds with a stable reporter cell line transfected with a plasmid comprising a CMV-promoter and a CMV-driven-luciferase gene flanked by 5'-untranslated regions (UTRs) and 3'-UTRs of mRNA of a human utrophin gene, comprising:
   i) administering a plurality of compounds to a plurality of stable reporter cell lines in a first plurality of microplates;
   ii) administering a positive control compound to the stable reporter cell lines in a second plurality of microplates and administering a negative control compound to the stable reporter cell lines in a third plurality of microplates;
   iii) incubating each of the plurality of stable reporter cell lines of (i) and (ii), respectively; and
   iv) measuring luminescence to assay for luciferase expression by the incubated stable reporter cell lines of (iii) after incubation; wherein a comparable or increased light emission by the stable reporter cell lines incubated with the plurality of compounds of (i) compared to light emission by the stable reporter cell lines incubated with the positive control compound of (ii) indicates luciferase expression, thereby identifying one or more compound of the plurality of compounds of (i) as either activating the CMV promoter or increasing overall synthesis of mRNA, and;

b) counter-screening, in parallel with or after the screening step (a), the plurality of compounds with a cell line stably transfected with a plasmid comprising only the CMV-promoter and the CMV-driven luciferase gene, comprising:

v) administering the plurality of compounds administered in step (i) to the stable reporter cell lines in the first plurality of microplates;

vi) administering the positive control compound to the stable reporter cell lines in the second plurality of microplates and administering the negative control compound to the stable reporter cell lines in the third plurality of microplates;

vi) incubating the stable reporter cell line of (v) and (vi); and vii) assaying for luciferase expression by the incubated the stable reporter cell lines of (vi) after incubation; wherein a comparable or an increased light emission by the stable reporter cell lines incubated with the plurality of compounds of (v) compared to light emission by the stable reporter cell lines incubated with the positive control compound of (vi) indicates luciferase expression, thereby identifying one or more compound of the plurality of compounds of (v) as only activating the CMV promoter; and viii) eliminating the one or more compound of the plurality of compounds identified in step (vi) as activating the CMV promoter only from the one or more compound of the plurality of compounds identified in step (iv) as either activating the CMV promoter or increasing overall synthesis of mRNA, thereby identifying post-transcriptional utrophin upregulator compounds.

BRIEF DESCRIPTION OF THE DRAWINGS

FIG. 1A is a diagram of the screening and counter screening constructs used to generate the stable $C_2C_{12}$-based assays used, as described herein. FIG. 1B shows the experimental strategy, as described herein: cells were plated in 384-well plates and allowed to attach for 24 hours, then treated with compounds and incubated for 24 hours before assaying luciferase activity. FIG. 1C shows a Scatter plot of Normalized Percent Activation (NPAc=$(DMSO_{avg}-Test\ well)/(DMSO_{avg}-Panobinostat_{avg})\times100$) for each compound, assayed at 1 μM concentrations. NPAc was used instead of Z-scores when comparing different conditions (e.g., dosages) for the same assay. FIG. 1D shows a Scatterplot comparing the NPAc at 0.1 μM and 1 μM for the 27 hits. Large circles indicate molecules active at both concentrations. Inset: Venn diagram of the number of hits identified at the two concentrations tested. FIG. 1E shows a Scatter plot of NPAc for the different compounds assayed at 1 μM concentrations, organized into different target classes.

FIG. 2A shows a Heatmap representation of dose-response traces for the 27 hit molecules. Clustering over rows was obtained by complete linkage with Euclidean distance measurements. The table (FIG. 2A) summarizes the $EC_{50}$ values calculated from the modeled logistic 4-parameter dose-response fits, as well as the ratio between $EC_{50}$ screen and $EC_{50}$ counter (Fold difference). FIG. 2B shows fitted dose-response curves organized by clusters. FIG. 2C shows a pipeline for the calculation of the H2LPS, with the example of TSA (S1045). FIG. 2D shows representative utrophin western-blot validation in $C_2C_{12}$ cells of the small molecules with the top 10 H2LPS, administered at 1 μM for 24 hours. The experiment was repeated 3 independent times. FIG. 2E shows quantification of average utrophin protein levels from western-blot validation. Values are mean and standard error of the mean of three independent experiments with three replicates for each molecule. *$p<0.05$; $p<0.01$; *$p<0.001$.

FIG. 3A shows dose-response traces (also called "curves" or "profiles" herein) of Z-scores for S1045 on the screening and counterscreening assays. For comparison purposes, both traces are normalized to 100%, without affecting their $EC_{50}$. FIG. 3B shows utrophin western-blot of $C_2C_{12}$ cells treated for 24 hours with increasing concentrations of TSA, and quantification FIG. 3C shows a dose-response screening curve fitted with dr4p1 to calculate the $EC_{50}$ for the utrophin protein levels. Values are mean and standard error of the mean.

FIG. 4A shows body weight monitored during TSA treatment [n=12/group]. FIG. 4B shows utrophin mRNA [n=5 ctrl and 6 treated] and FIG. 4C shows utrophin protein [n=3/group] levels in TA (Tibialis Anterior) muscle after TSA treatment. FIG. 4D shows rotarod performance test after TSA treatment [n=12/group]. FIG. 4E shows Twitch [n=18 muscles/group] and FIG. 4F shows tetanic [n=18 muscles/group] specific forces, respectively, of EDL (Extensor Digitorum Longus) muscles after TSA treatment. FIG. 4G shows EDL muscles force decrement after 5 consecutive eccentric contractions (ECCs) in the EDL muscle. Values are mean and standard error of the mean. *$p<0.05$.

FIG. 5A shows cell viability (ATP) and luciferase activity following 24 hours incubation with increasing DMSO concentrations. FIG. 5B shows luciferase activity and FIG. 5C shows cell viability at different plating densities and incubation times, respectively. Linear fit demonstrated the linearity of response as a function of cell density. FIG. 5D shows Panobinostat dose-response using the screening and counterscreening assays. FIG. 5E shows a Scatter plot of Normalized Percent Activation (NPAc) for each compound, assayed at 0.1 μM concentrations. FIG. 5F shows a Scatter plot of NPAc for the different compounds assayed at 0.1 μM concentrations, organized into different target classes. Values are mean and standard error of the mean.

RLUs) of the stable $C_2C_{12}$-cells treated with Panobinostat, which was a 100-fold increase over the basal signal.

Figure 9:
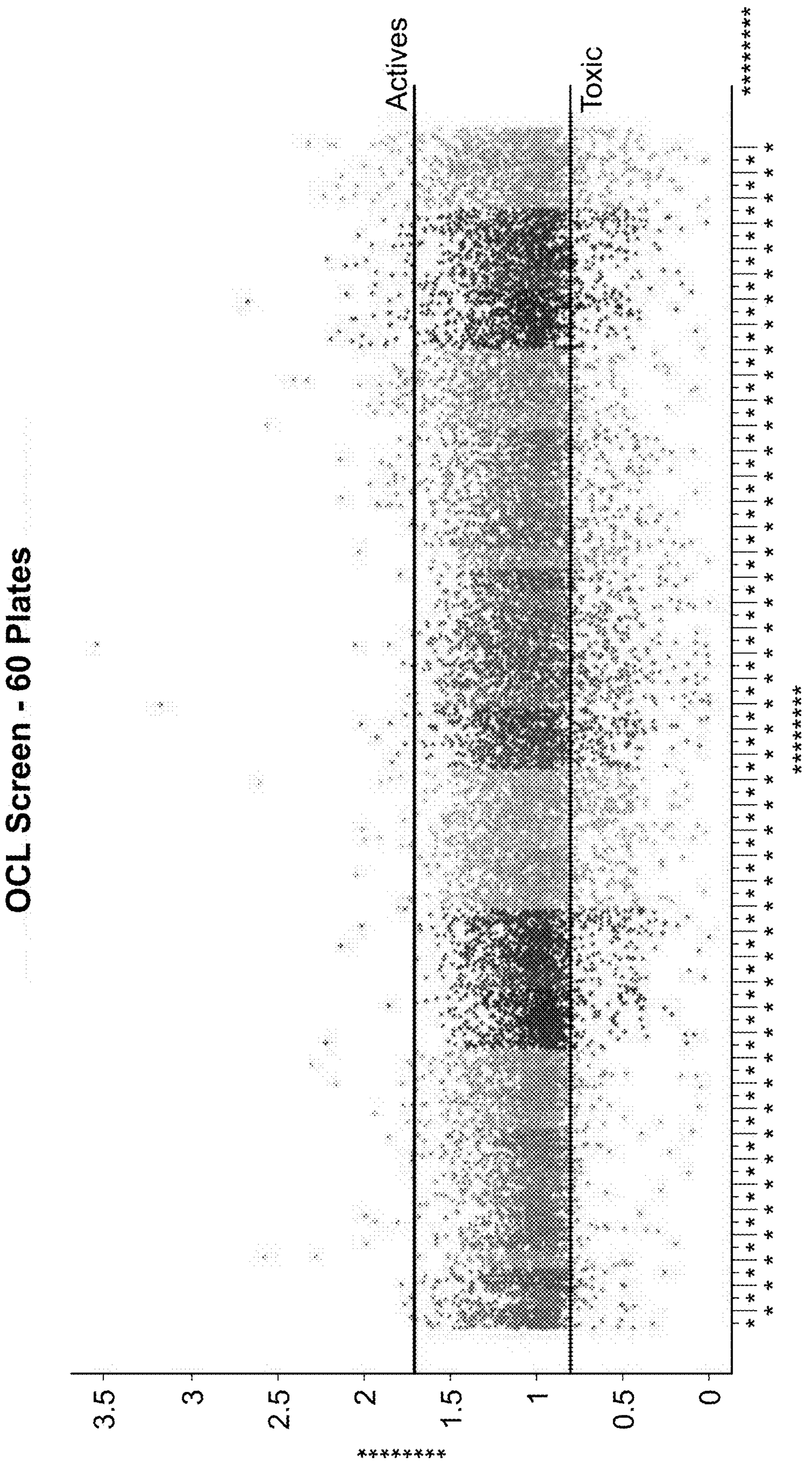

FIG. 9 shows candidate hits of an OCL (orthogonally compressed Library collection from The Lankenau Institute for Medical Research) screen using 60 plates, shown as row number to assay plate well. Active compound are shown above, and cytotoxic compounds are shown below.

FIG. 10 shows screen statistics for the OCL screen in FIG. 9.

Figure 11:
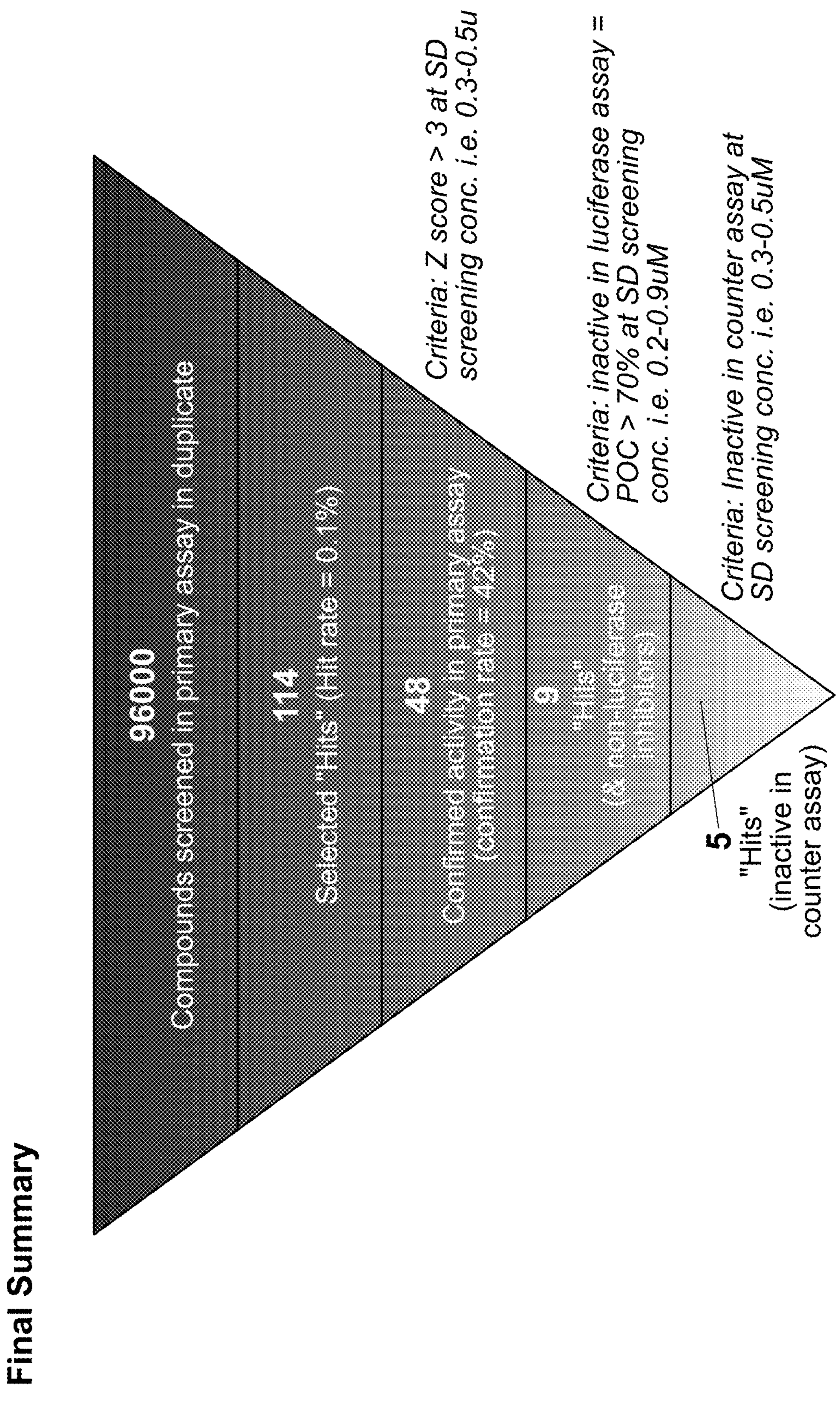
Figure 12A:
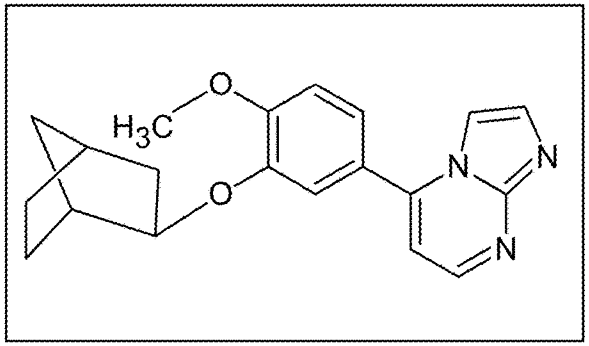
Figure 12A:
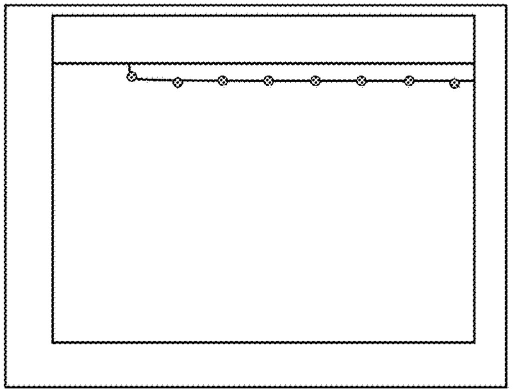
Figure 12A:
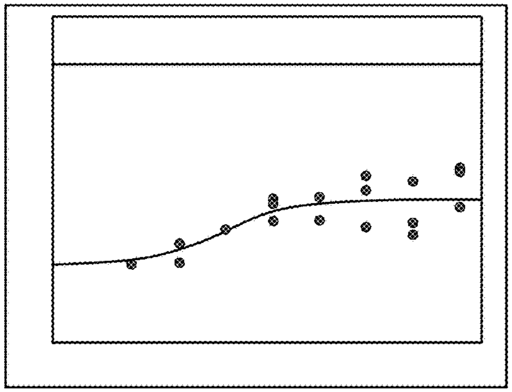
Figure 12A:
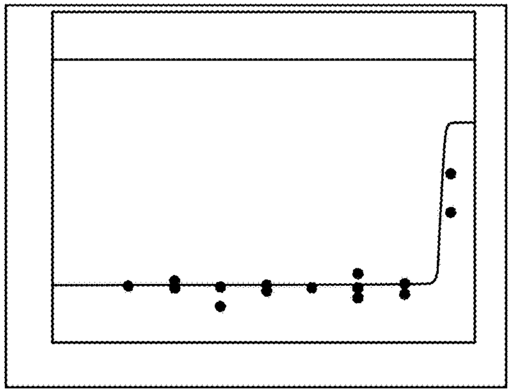
Figure 12B:
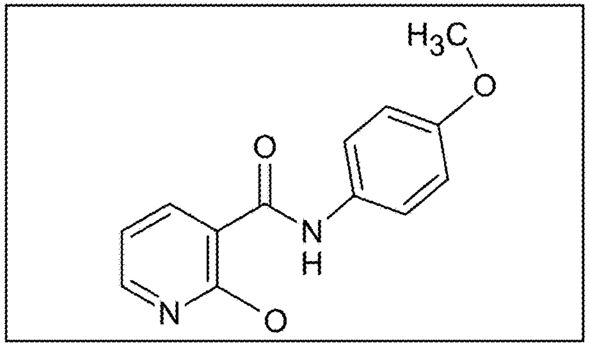
Figure 12B:
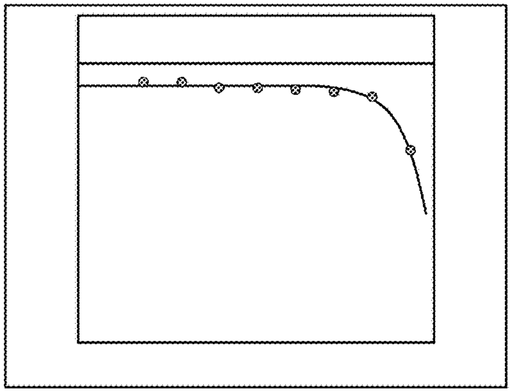
Figure 12B:
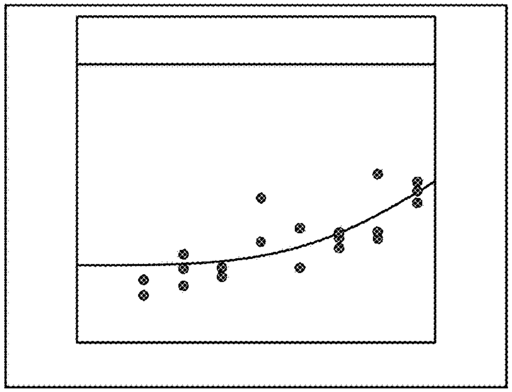
Figure 12B:
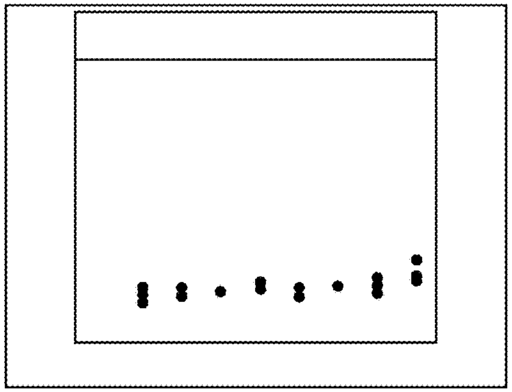
Figure 12C:
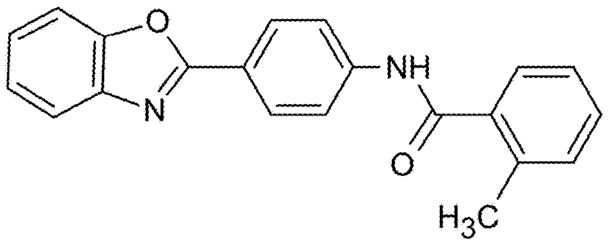
Figure 12C:
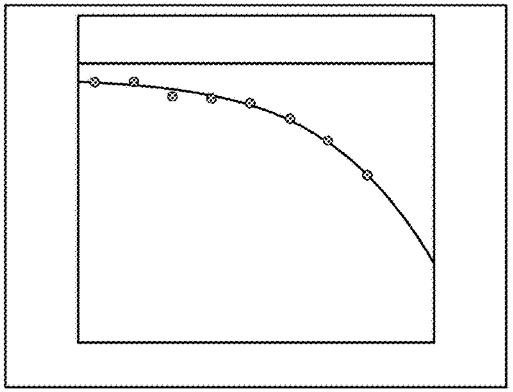
Figure 12C:
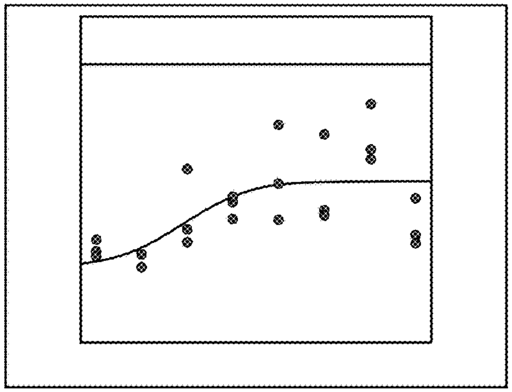
Figure 12C:
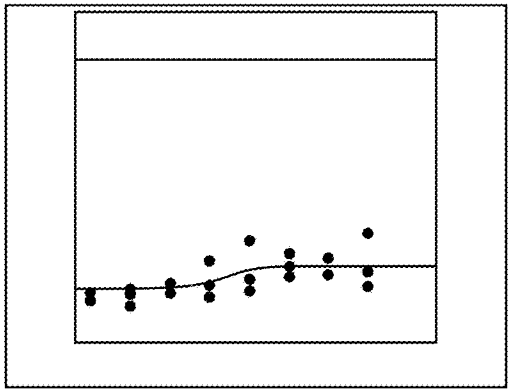
Figure 12D:
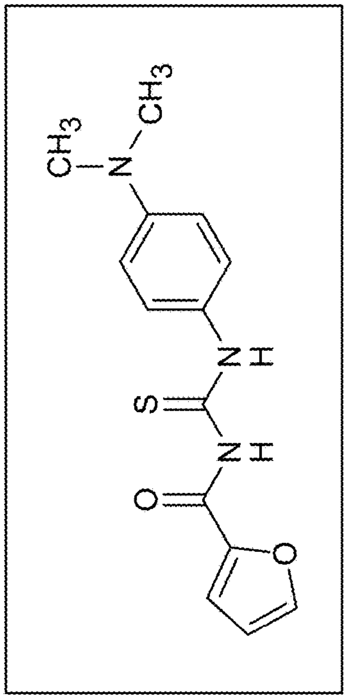
Figure 12D:
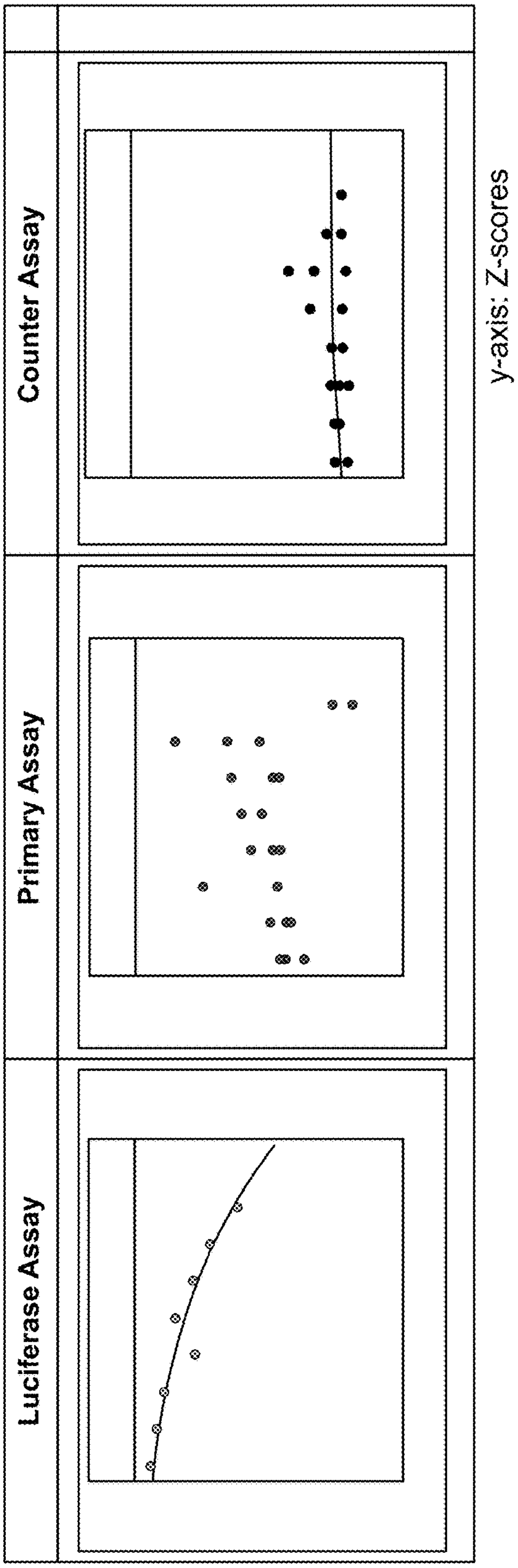
Figure 12E:
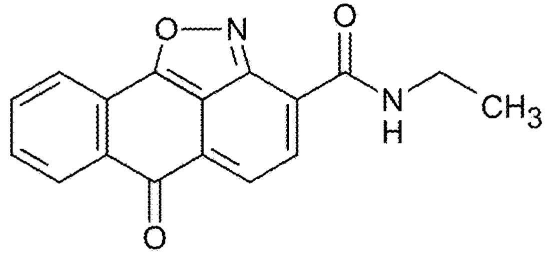
Figure 12E:
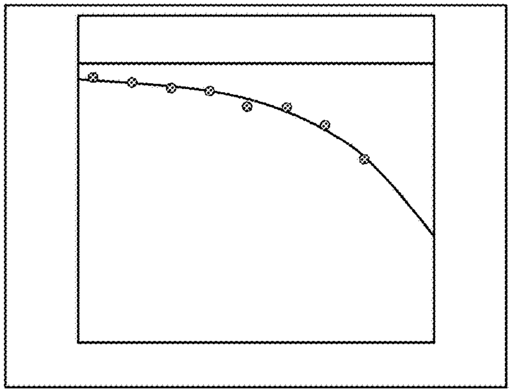
Figure 12E:
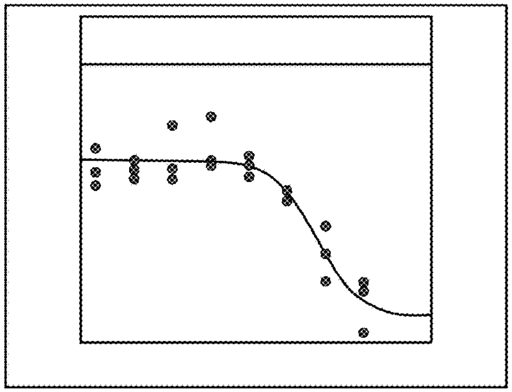
Figure 12E:
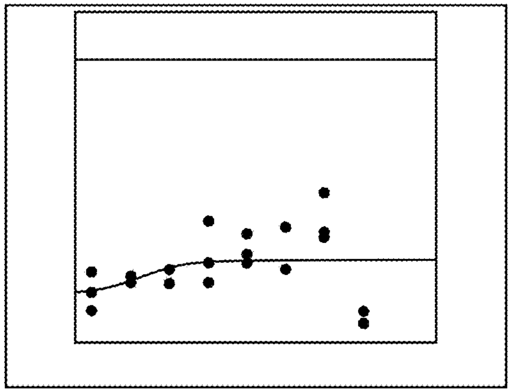

FIG. 11 shows the HTSC screening of 96,000 compounds in a primary screening assay (OCL screen) and the selection of hit compounds ("hits").

FIG. 12 shows the five selected hits selected in FIG. 11, including product name, chemical structure, luciferase assay, primary assay and counter assay. Y-axis: Z-scores and x-axis: concentration (μM).

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Upregulation of endogenous utrophin offers great promise for treating DMD, as it can functionally compensate for the lack of dystrophin caused by DMD gene mutations without the immunogenic concerns associated with delivering dystrophin. However, post-transcriptional repression mechanisms targeting the 5' and 3'-untranslated regions (UTRs) of utrophin mRNA significantly limit the magnitude of utrophin upregulation achievable by promoter activation.

The present invention provides an alternate strategy for a DMD-specific therapy that in principle is applicable to all patients, i.e., not limited to restricted subsets of patients having mutation-specific DMDs, which is to increase the expression of the autosomal-encoded dystrophin-related protein homolog, utrophin. Like dystrophin, utrophin (also known as dystrophin-related protein-DRP) is a member of the spectrin superfamily and shares extensive sequence similarity and functional motifs with dystrophin, including the capacity to bind the same dystrophin associated glycoprotein complex. Utrophin is expressed at high levels in fetal tissue and developmentally downregulated in adults. In the mdx mouse model of DMD the developmentally-regulated decline in utrophin levels corresponds with the onset of muscle necrosis. Expression of truncated or full-length utrophin significantly ameliorates the phenotype of mdx mice and provides the rationale for harnessing pharmacological upregulation of endogenous utrophin as a therapeutic strategy for DMD.

The molecules and mechanisms regulating utrophin expression have been the subject of detailed mapping and characterization, in part to determine mechanisms that could be targeted to drive utrophin upregulation for DMD. Utrophin has a broad tissue distribution and has a number of isoforms driven by distinct promoters. The Utrophin A isoform is the predominant isoform expressed in muscle and hence, has been the subject of concerted studies that have mapped the major regulatory motifs and validated trans-activating and repressing factors. Unfortunately, despite these intense efforts, none are currently clinically applicable because of the limited magnitude of upregulation achieved so far by targeting the promoter. This has been recognized to be, at least in part, due to the fact that regulation of utrophin expression is more complex than previously appreciated. Hence, promoter trans-activating molecules may not suffice as therapeutics themselves. Detailed molecular analyses of utrophin mRNA and protein expression have demonstrated that utrophin is subject to significant post-transcriptional regulation, as exemplified by the transcription-translation mismatch in developing muscle cells, in different muscle groups as well as in the CNS. Importantly, a variety of mechanisms targeting the 5' and 3' UTRs of the utrophin mRNA significantly contribute to repressing utrophin protein expression in adult muscle. The 5' UTR contains a putative IRES site and been shown to be important for regulation of utrophin protein levels during regeneration and in response to steroids. Additionally, two cis-acting elements, along with a short ORF, have been found in the 5'-UTR and have been suggested to repress cap dependent translation. The 3' UTR contains a series of conserved AU-rich elements (AREs) as well as multiple miRNA binding sites that provide an additional layer of regulation. It has been shown that the interaction between utrophin mRNA and miRNAs can be targeted to upregulate utrophin expression in vitro and in vivo to upregulate utrophin and ameliorate the dystrophic phenotype. Together, these studies provide a strong rationale for one aspect of the present invention, methods for identifying small molecules (compounds) capable of interacting with the 5' and/or 3'UTR to upregulate utrophin expression.

A stable reporter cell line containing the luciferase gene flanked by the 5' and 3'-UTR regions of the human utrophin gene has been developed, as described by Moorwood, C., et al., *J Biomol Screen* 18.400-406 (2013), which is incorporated herein by reference in its entirety. In the present study, as described in the Examples herein, this assay has been used together with a counterassay to screen a small molecule library of 3127 small molecules that includes~1000 FDA approved drugs.

In one aspect, this invention provides a method for increasing expression of utrophin in a subject in need thereof, the method comprising administering to the subject a pharmaceutical composition comprising a post-transcriptionally utrophin upregulator compound. In an embodiment of the herein provided method, the subject has a muscular dystrophy. In another embodiment, the muscular dystrophy is Duchenne Muscular Dystrophy (DMD). In a further embodiment, the muscular dystrophy is Becker muscular dystrophy (BMD). In certain embodiments of the herein provided method, the post-transcriptionally utrophin upregulator compound is histone deacetylase (HDAC) inhibitor Trichostatin A (TSA) having a chemical structure of:

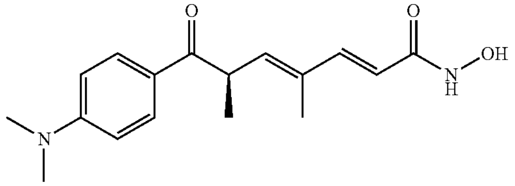 [SMILES: CC(/C=C/C(=O)NO)=C\[C@@H](C)C(=O)c1ccc(N(C)C)cc1]

In some embodiments, the post-transcriptionally utrophin upregulator compound is HDAC inhibitor AR-42 having a chemical structure of:

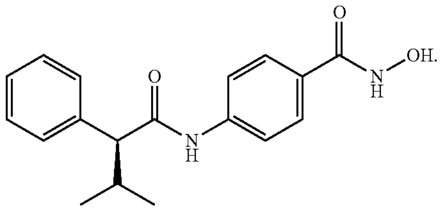 [SMILES: CC(C)[C@H](C(=O)Nc1ccc(C(=O)NO)cc1)c1ccccc1]

In certain embodiments, the post-transcriptionally utrophin upregulator compound is HDAC inhibitor Pracinostat having a chemical structure of:

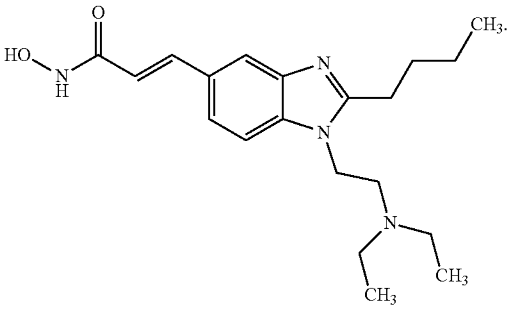 [SMILES: CCCCc1nc2cc(/C=C/C(=O)NO)ccc2n1CCN(CC)CC]

In an embodiment, the post-transcriptionally utrophin upregulator compound is pan-HDAC inhibitor Abexinostat (PCI-24781) having a chemical structure of:

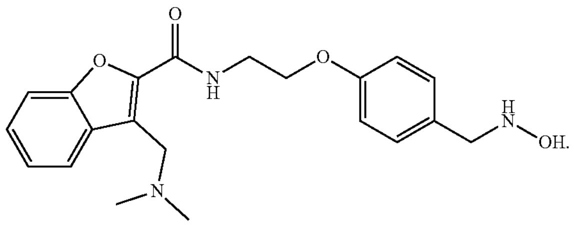 [SMILES: CN(C)Cc1c(C(=O)NCCOc2ccc(CNO)cc2)oc2ccccc12]

In another embodiment, the post-transcriptionally utrophin upregulator compound is HDAC inhibitor Belinostat (PXD101) having a chemical structure of:

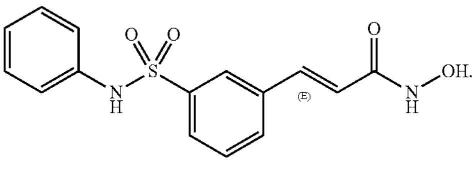 [SMILES: O=C(/C=C/c1cccc(S(=O)(=O)Nc2ccccc2)c1)NO]

In some embodiments, the post-transcriptionally utrophin upregulator compound is HDAC inhibitor LMK-235 having a chemical structure of:

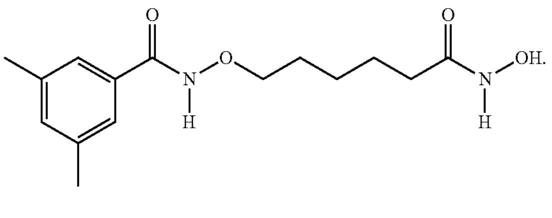 [SMILES: Cc1cc(C)cc(C(=O)NOCCCCCC(=O)NO)c1]

In certain embodiments, the post-transcriptionally utrophin upregulator compound is pan-HDAC inhibitor Panobinostat (LBH589) having a chemical structure of:

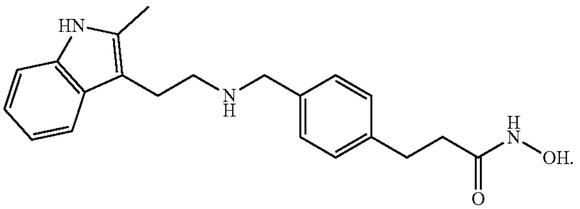 [SMILES: Cc1[nH]c2ccccc2c1CCNCc1ccc(CCC(=O)NO)cc1]

In various embodiments, the post-transcriptionally utrophin upregulator compound is HDAC inhibitor Givinostat having a chemical structure of:

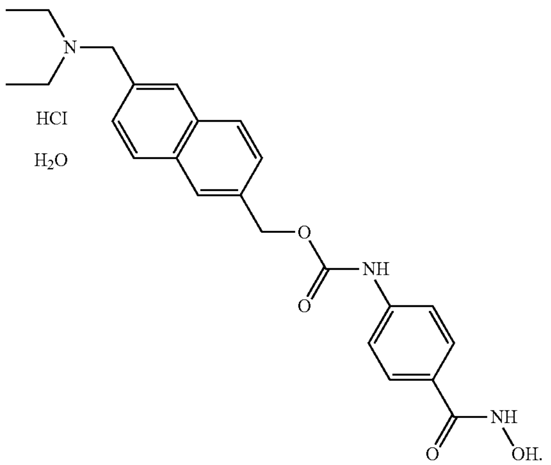

In some embodiments, the post-transcriptionally utrophin upregulator compound is a compound having a chemical structure of:

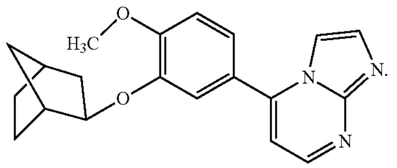 [SMILES: COc1ccc(-c2ccnc3nccn23)cc1OC1CC2CCC1C2]

In an embodiment, the post-transcriptionally utrophin upregulator compound is a compound having a chemical structure of:

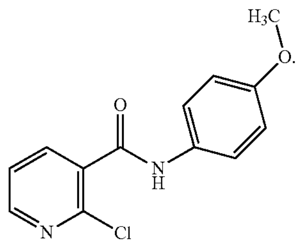 [SMILES: COc1ccc(NC(=O)c2cccnc2Cl)cc1]

In various embodiments, the post-transcriptionally utrophin upregulator compound is a compound having a chemical structure of:

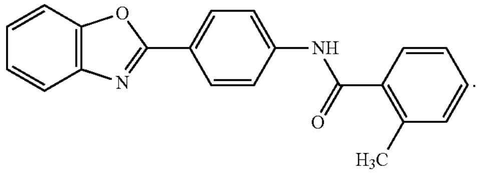 [SMILES: Cc1ccccc1C(=O)Nc1ccc(-c2nc3ccccc3o2)cc1]

In certain embodiments, the post-transcriptionally utrophin upregulator compound is a compound having a chemical structure of:

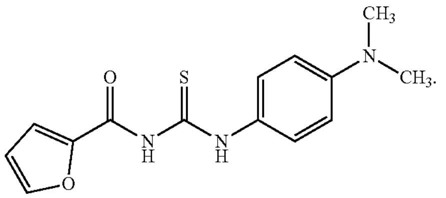 [SMILES: CN(C)c1ccc(NC(=S)NC(=O)c2ccco2)cc1]

In another embodiment, the post-transcriptionally utrophin upregulator compound is a compound having a chemical structure of:

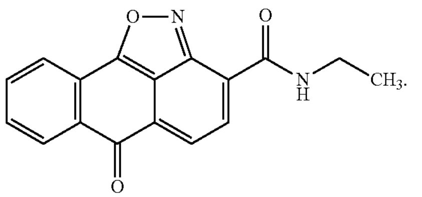 [SMILES: CCNC(=O)c1ccc2c3c(onc13)-c1ccccc1C2=O]

In another aspect, this invention provides a method for improving a dystrophic phenotype in a muscle of a subject having loss or reduction of dystrophin protein expression, the method comprising administering to the subject a pharmaceutical composition comprising a post-transcriptionally utrophin upregulator compound. In an embodiment of the herein provided method, the loss or reduction of dystrophin protein expression is caused by a dystrophin gene mutation. In some embodiments, the improved dystrophic phenotype is muscle function and/or performance. In certain embodiments, the muscle function and/or performance is motor coordination, postural control, muscle fatigability, muscle contractility and tetanic strength. In particular embodiments, the improved dystrophic phenotype is a muscle structure. In an embodiment, the muscle structure is a lower number of centrally nucleated fibers and/or an increased muscle mass. In some embodiments, the improved dystrophic phenotype is a decreased susceptibility of muscle to damage caused by repeated eccentric muscle contractions (ECC). In certain embodiments, wherein the improved dystrophic phenotype is decreased muscle wasting. In some embodiments, the decreased muscle wasting is necrosis and/or atrophy. In an embodiment, the post-transcriptionally utrophin upregulator compound is histone deacetylase (HDAC) inhibitor Trichostatin A (TSA). In another embodiment, the post-transcriptionally utrophin upregulator compound is HDAC inhibitor AR-42. In some embodiments, the post-transcriptionally utrophin upregulator compound is HDAC inhibitor Pracinostat. In certain embodiments, the post-transcriptionally utrophin upregulator compound is pan-HDAC inhibitor Abexinostat (PCI-24781). In some embodiments, the post-transcriptionally utrophin upregulator compound is HDAC inhibitor Belinostat (PXD101). In particular embodiments, the post-transcriptionally utrophin upregulator compound is HDAC inhibitor LMK-235. In various embodiments, the post-transcriptionally utrophin upregulator compound is pan-HDAC inhibitor Panobinostat (LBH589).

In some embodiments, the post-transcriptionally utrophin upregulator compound is a compound Givinostat.

In certain embodiments, the post-transcriptionally utrophin upregulator compound is HDAC inhibitor having a chemical structure of:

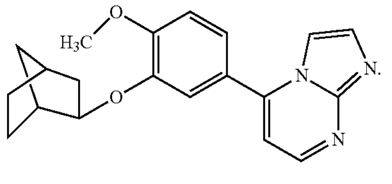 [SMILES: COc1ccc(-c2ccnc3nccn23)cc1OC1CC2CCC1C2]

In various embodiments, the post-transcriptionally utrophin upregulator compound is a compound having a chemical structure of:

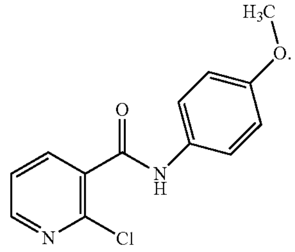 [SMILES: COc1ccc(NC(=O)c2cccnc2Cl)cc1]

In some embodiments, the post-transcriptionally utrophin upregulator compound is a compound having a chemical structure of:

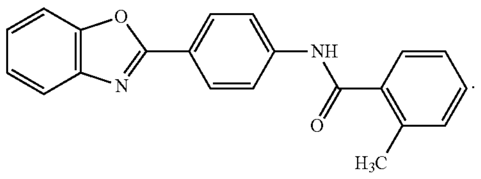 [SMILES: Cc1ccccc1C(=O)Nc1ccc(-c2nc3ccccc3o2)cc1]

In further embodiments, the post-transcriptionally utrophin upregulator compound is a compound having a chemical structure of:

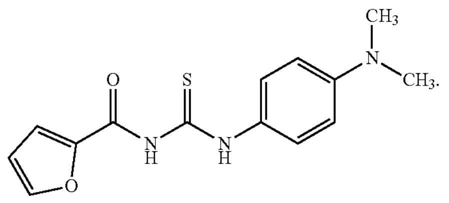 [SMILES: CN(C)c1ccc(NC(=S)NC(=O)c2ccco2)cc1]

In some embodiments, the post-transcriptionally utrophin upregulator compound is a compound having a chemical structure of:

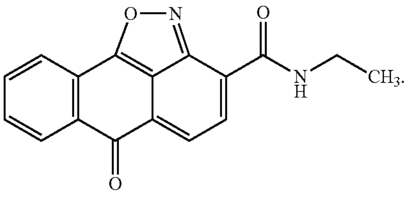 [SMILES: CCNC(=O)c1ccc2c3c(onc13)-c1ccccc1C2=O]

In a specific embodiment, the subject has a muscular dystrophy. In an embodiment, the muscular dystrophy is DMD. In another embodiment, the muscular dystrophy is BMD.

In one aspect, this invention provides a method for treating and preventing muscle wasting caused by a lack or reduced expression of dystrophin protein in a subject, the method comprising administering to the subject a pharmaceutical composition comprising a post-transcriptionally utrophin upregulator compound. In certain embodiments of the herein provided method, the lack or reduced expression of dystrophin protein is caused by a dystrophin gene mutation. In some embodiments, the post-transcriptionally utrophin upregulator compound is histone deacetylase (HDAC) inhibitor Trichostatin A (TSA). In various embodiments, the post-transcriptionally utrophin upregulator compound is HDAC inhibitor AR-42. In some embodiments, the post-transcriptionally utrophin upregulator compound is HDAC inhibitor Pracinostat. In certain embodiments, the post-transcriptionally utrophin upregulator compound is pan-HDAC inhibitor Abexinostat (PCI-24781). In a specific embodiment, the post-transcriptionally utrophin upregulator compound is HDAC inhibitor Belinostat (PXD101). In another embodiment, the post-transcriptionally utrophin upregulator compound is HDAC inhibitor LMK-235. In some embodiments, the post-transcriptionally utrophin upregulator compound is pan-HDAC inhibitor Panobinostat (LBH589). In further embodiments, the post-transcriptionally utrophin upregulator compound is HDAC inhibitor Givinostat.

In certain embodiments, the post-transcriptionally utrophin upregulator compound is a compound having a chemical structure of:

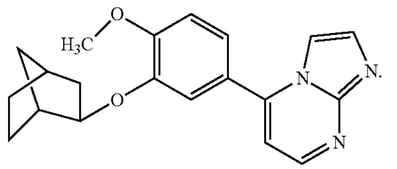 [SMILES: COc1ccc(-c2ccnc3nccn23)cc1OC1CC2CCC1C2]

In some embodiments, the post-transcriptionally utrophin upregulator compound is a compound having a chemical structure of:

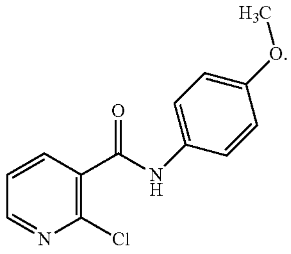 [SMILES: COc1ccc(NC(=O)c2cccnc2Cl)cc1]

In various embodiments, the post-transcriptionally utrophin upregulator compound is a compound having a chemical structure of:

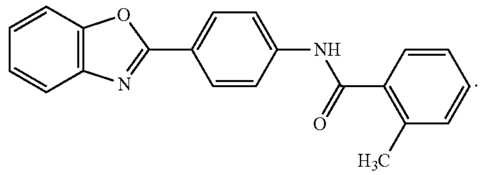 [SMILES: Cc1ccccc1C(=O)Nc1ccc(-c2nc3ccccc3o2)cc1]

In further embodiments, the post-transcriptionally utrophin upregulator compound is a compound having a chemical structure of:

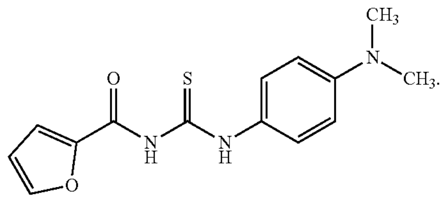 [SMILES: CN(C)c1ccc(NC(=S)NC(=O)c2ccco2)cc1]

In some embodiments, the post-transcriptionally utrophin upregulator compound is a compound having a chemical structure of:

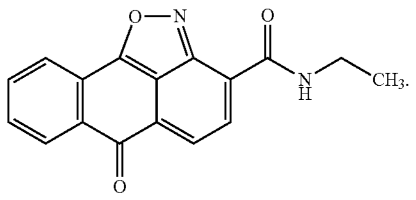 [SMILES: CCNC(=O)c1ccc2c3c(onc13)-c1ccccc1C2=O]

In another aspect, this invention provides a method for treating a subject having a muscular dystrophy, the method comprising administering to the subject a pharmaceutical composition comprising a post-transcriptionally utrophin upregulator compound. In certain embodiments of the herein provided method, the muscular dystrophy is caused by a dystrophin gene mutation. In some embodiments, the muscular dystrophy is DMD. In further embodiments, the muscular dystrophy is Becker muscular dystrophy (BMD). In certain embodiments, the post-transcriptionally utrophin upregulator compound is histone deacetylase (HDAC) inhibitor Trichostatin A (TSA). In some embodiments, the post-transcriptionally utrophin upregulator compound is HDAC inhibitor AR-42. In various embodiments, the post-transcriptionally utrophin upregulator compound is HDAC inhibitor Pracinostat. In some embodiments, the post-transcriptionally utrophin upregulator compound is pan-HDAC inhibitor Abexinostat (PCI-24781). In certain embodiments, the post-transcriptionally utrophin upregulator compound is HDAC inhibitor Belinostat (PXD101). In some embodiments, the post-transcriptionally utrophin upregulator compound is HDAC inhibitor LMK-235. In particular embodiments, the post-transcriptionally utrophin upregulator compound is pan-HDAC inhibitor Panobinostat (LBH589). In an embodiment, the post-transcriptionally utrophin upregulator compound is HDAC inhibitor Givinostat.

In some embodiments, the post-transcriptionally utrophin upregulator compound is a compound having a chemical structure of:

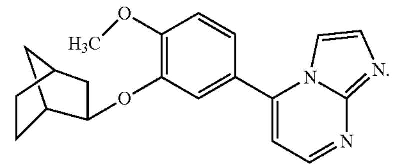 [SMILES: COc1ccc(-c2ccnc3nccn23)cc1OC1CC2CCC1C2]

In another embodiment, the post-transcriptionally utrophin upregulator compound is a compound having a chemical structure of:

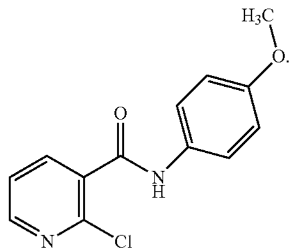 [SMILES: COc1ccc(NC(=O)c2cccnc2Cl)cc1]

In certain embodiments, the post-transcriptionally utrophin upregulator compound is a compound having a chemical structure of:

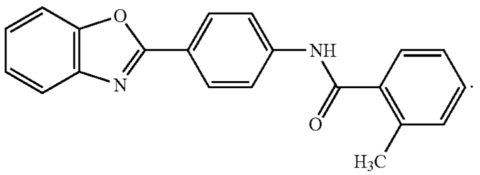

In various embodiments, the post-transcriptionally utrophin upregulator compound is a compound having a chemical structure of:

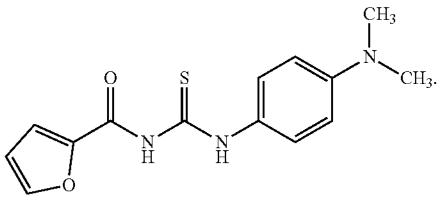 [SMILES: CN(C)c1ccc(NC(=S)NC(=O)c2ccco2)cc1]

In still another embodiment, the post-transcriptionally utrophin upregulator compound is a compound having a chemical structure of:

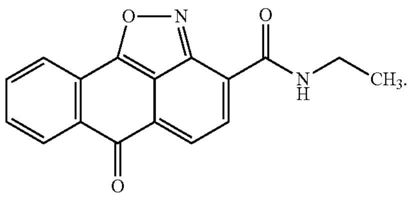 [SMILES: CCNC(=O)c1ccc2c3c(onc13)-c1ccccc1C2=O]

In one aspect, this invention provides a method for high-throughput screening for a post-transcriptional utrophin upregulator compounds, the method comprising:

a) screening a plurality of compounds with a stable reporter cell line transfected with a plasmid comprising a CMV-promoter and a CMV-driven-luciferase gene flanked by 5'-untranslated regions (UTRs) and 3'-UTRs of mRNA of a human utrophin gene, comprising:
   i) administering a plurality of compounds to a plurality of stable reporter cell lines in a first plurality of microplates;
   ii) administering a positive control compound to the stable reporter cell lines in a second plurality of microplates and administering a negative control compound to the stable reporter cell lines in a third plurality of microplates;
   iii) incubating each of the plurality of stable reporter cell lines of (i) and (ii), respectively; and
   iv) measuring luminescence to assay for luciferase expression by the incubated stable reporter cell lines of (iii) after incubation; wherein a comparable or increased light emission by the stable reporter cell lines incubated with the plurality of compounds of (i) compared to light emission by the stable reporter cell lines incubated with the positive control compound of (ii) indicates luciferase expression, thereby identifying one or more compound of the plurality of compounds of (i) as either activating the CMV promoter or increasing overall synthesis of mRNA, and;
b) counter-screening, in parallel with or after the screening step (a), the plurality of compounds with a cell line stably transfected with a plasmid comprising only the CMV-promoter and the CMV-driven luciferase gene, comprising:
   v) administering the plurality of compounds administered in step (i) to the stable reporter cell lines in a first plurality of microplates;

vi) administering the positive control compound to the stable reporter cell lines in a second plurality of microplates and administering the negative control compound to the stable reporter cell lines in a third plurality of microplates;

vi) incubating the stable reporter cell lines of (v) and (vi); and vii) assaying for luciferase expression by the incubated stable reporter cell lines of (vi) after incubation; wherein a comparable or an increased light emission by the stable reporter cell lines incubated with the plurality of compounds of (v) compared to light emission by the stable reporter cell lines incubated with the positive control compound of (vi) indicates luciferase expression, thereby identifying one or more compound of the plurality of compounds of (v) as only activating the CMV promoter; and viii) eliminating the one or more compound of the plurality of compounds identified in step (vii) as activating the CMV promoter only from the one or more compound of the plurality of compounds identified in step (iv) as either activating the CMV promoter or increasing overall synthesis of mRNA, thereby identifying post-transcriptional utrophin upregulator compounds.

In an embodiment, the method for high-throughput screening for post-transcriptional utrophin upregulator compounds further comprises:

1) aggregating data from the incubated stable reporter cell lines administered the positive and the negative control compound;

2) calculating z'-factors as follows: $[1-(3^*(DMSO_{sd}+Panobinostat_{sd})/Abs(DMSO_{avg}—Panobinostat_{avg}))]$ for each assay plate of the second and third plurality of microplates, as a measure of assay performance and data quality, wherein a z'-factor>0.5 represents acceptable data;

3) normalizing raw data values of the stable reporter cell lines incubated with the plurality of compounds of (i) to aggregating data from the incubated stable reporter cell lines administered the positive and the negative control compound;

4) expressing the normalized data as Normalized Percent Activation $[NPAc=((DMSO_{avg}-Test\ well)/(DMSO_{avg}-Panobinostat_{avg}))\times 100]$ and Z-score $[Z=(Test\ well-DMSO_{avg})/(DMSO_{sd})]$; and 5) setting a hit-rate cutoff of 22.07% activation calculated as (3*Stdev[NPAc])+Avg[NPAc], 6) identifying one or more compound of the plurality of compounds identified in step (viii) as a hit, wherein Panobinostat is the positive control compound and DMSO is the negative control compound.

In an embodiment, the method further comprises Scatter plotting of the Normalized Percent Activation (NPAc) for the stable reporter cell lines incubated with the plurality of compounds of (i).

In another embodiment, the method further comprises performing a dose-dependent analysis of the one or more compound of the plurality of compounds identified in step (viii) at a plurality of concentrations of the one or more compound and plotting fitted dose-response profiles for the plurality of concentrations of the compounds. In an embodiment, the method further comprises grouping organizing the fitted plotted dose-response profiles into clusters of one or more compound of the plurality of compounds having similar dose-response profiles.

In some embodiments, the method further comprises computing Hit 2 Lead Performance Score (H2LPS) of individual hits, wherein the computing includes accounting for values for parameters (i) difference between $EC_{50}$ determined in screening and counterscreening, (ii) dose-dependent behavior of each of the fitted dose-response profiles and (iii) amplitude of each fitted dose-response profiles, wherein the H2LPS equals to 0 when unacceptable values for one or more of parameters (i)-(iii) are determined, wherein the unacceptable values comprise no dose-dependence or similar $EC_{50}$ between screening and counterscreening;

wherein computing of the H2LPS prioritizes the one or more compound of the plurality of compounds identified in step (viii) having a satisfactory dose-response profile, a low $EC_{50}$ and high specificity, calculated as the fold difference between the $EC_{50}$s from screening of step (a) and counterscreening of step (b), wherein the H2LPS>0 for a hit compound.

In an embodiment, the method further comprises performing in vitro validation with a plurality of highest hit compounds to determine utrophin expression levels for each of the highest hit compounds. In another embodiment of the herein provided method, the post-transcriptional utrophin upregulator compounds reduce and/or prevent post-transcriptional repression of utrophin expression at 5'- and/or 3'-untranslated regions (UTRs) of utrophin mRNA.

In some embodiments, the method further comprises ranking the one or more compound identified as a hit in step (6) according to an automated Hit 2 Lead Performance Score (H2LPS). In certain embodiments, the method further comprises further evaluating the ranked compound for utrophin upregulation. In a particular embodiment of the method for high-throughput screening for a post-transcriptional utrophin upregulator compounds, steps (1)-(6) are performed on a computer having: a. a processor; b. a memory storing: (i) aggregate data from the incubated stable reporter cell line administered the positive and the negative control compound, respectively; (ii) calculated z'-factors the positive and the negative control compound, respectively; (iii) normalized data as Normalized Percent Activation; (iv) data values of the stable reporter cell lines incubated with the plurality of compounds of (i) and/or incubated with the plurality of compounds of step (viii); which, when executed, configure the processor to (A) calculate activity as follows: (3*Stdev[NPAc])+Avg[NPAc], and (B) identify one or more compound of the plurality of compounds identified in step (viii) as a hit when the calculated activity is 22.07% or greater.

Also developed and applied, as described herein, is a two-step pipeline which uses cluster analysis to group small molecules with similar activity profiles, and then ranked them according to an automated Hit 2 Lead Performance Score (H2LPS) based on efficacy, potency and specificity. The small molecules were ranked according to the H2LPS and the top 10 small molecules (compounds) were validated using orthogonal assays for endogenous utrophin expression in vitro. Evaluation of the top scoring hit in the mdx mouse model of DMD increased utrophin expression and resulted in functional improvement of the dystrophic phenotype. This study validates the herein described screening assay paradigm for post-transcriptional utrophin up-regulators, including application of an automated scoring methodology, which can be applied to larger compound libraries thereby potentially identifying additional novel starting points for DMD therapeutic development.

EXAMPLES

Example 1

Screening and Counterscreening Cell Lines and HTS Implementation

The construct for the HTS assay was generated by cloning the 5'- and 3'-UTRs of human utrophin into pGL4:50-hygro (Promega, Madison, WI) at the 5' and 3' of the luciferase coding sequence and has been described previously by Moorwood. C., et al., J Biomol Screen 18, 400-406 (2013), which is incorporated herein by reference in its entirety. For the counterscreening assay, the pGL4:50-hygro plasmid was used alone. Low passage $C_2C_{12}$ cells obtained from ATCC were transfected with either constructs, stably selected with 500 μg/mL hygromycin and subcloned using two rounds of serial dilutions to isolate single cell-derived colonies in a 96 wells plate format. Stable clones were tested to verify the presence of the transgene, luciferase activity and absence of mycoplasma. The selected clones were cultured in presence of 100 μg/mL hygromycin B and were transferred to the HTS Facility at the University of Pennsylvania for implementation into a 384-wells format suitable for HTS. Technical data for the screening lines are reported in Table 1.

TABLE 1

Screening technical data.

| | Selleckchem screening @ 0.1 mM | Selleckchem screening @ 1 mM | Selleckchem dose-response screening |
|---|---|---|---|
| # plates | 10 | 10 | 1 |
| # compounds tested | 3127 | 3127 | 27 |
| S/B CV % between plates | 7.10 | 2.83 | 10.68 |
| Z' Factor | 0.63 | 0.69 | 0.75 |
| CV % negative | 7.9 | 10.51 | 7.96 |
| CV % positive | 6.35 | 7.05 | 5.29 |
| Hit-rate | 0.90% | | 48% |

Results of Implementation of the Cell-Based High-Throughput Screening

Figure 1A:
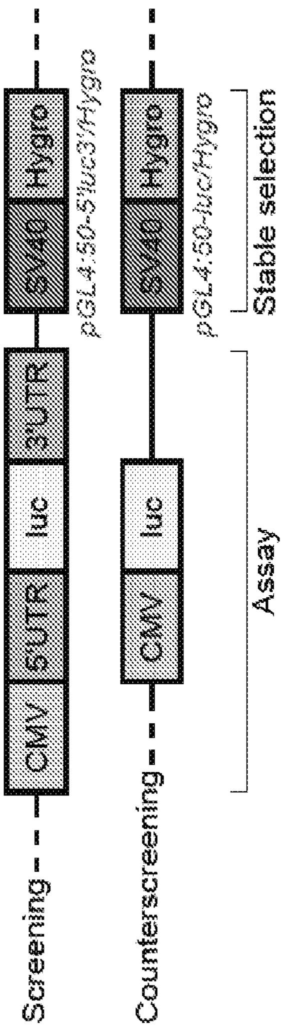
FIGS. 1A-1E show High-Throughput Screening implementation.
Figure 1B:
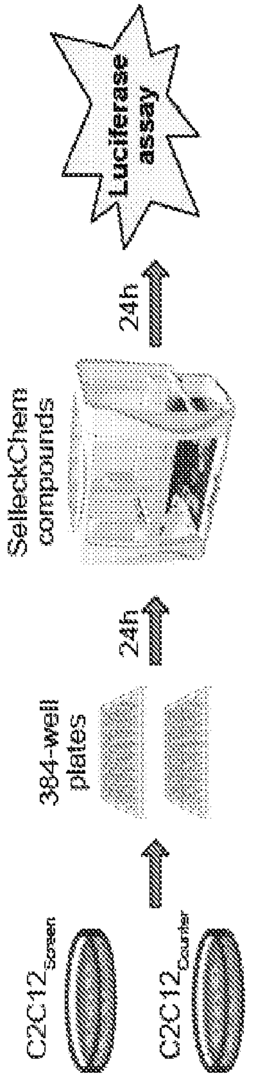
Figure 5A:
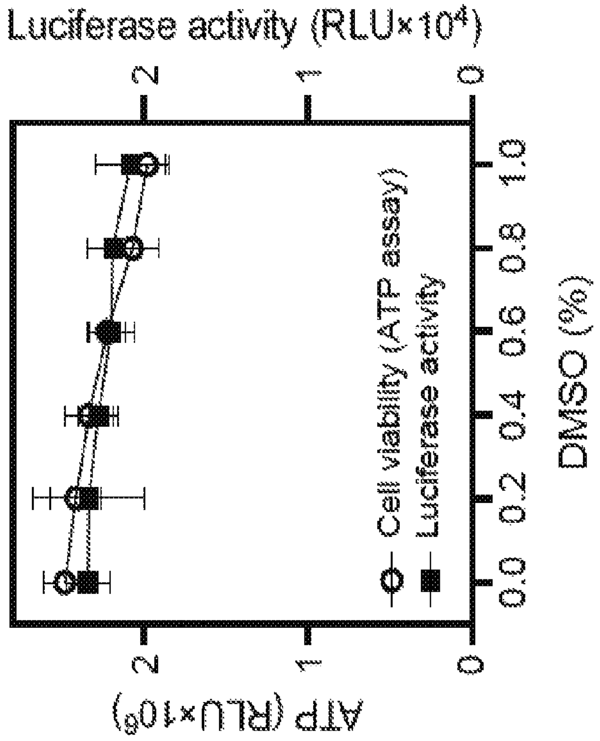
FIGS. 5A-5F show technical validation of the high-throughput screening cell line.
Figure 5B:
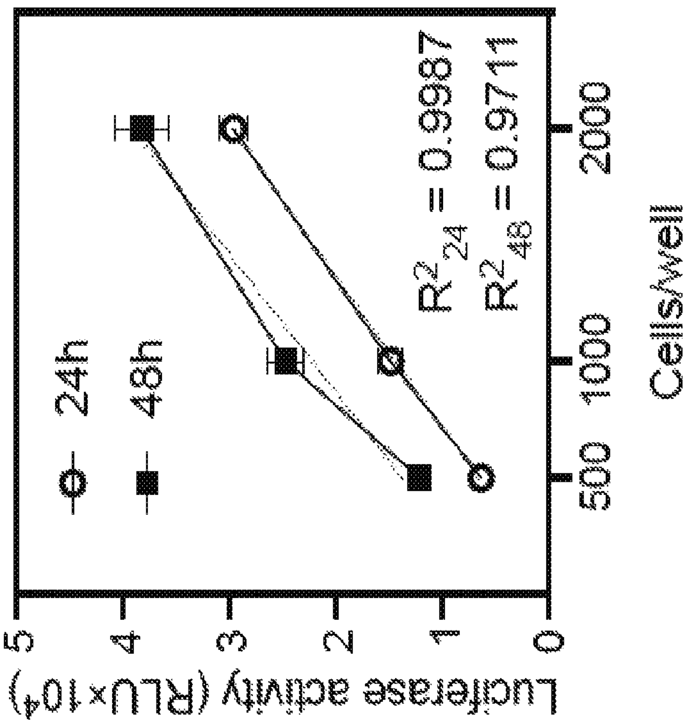
Figure 5C:
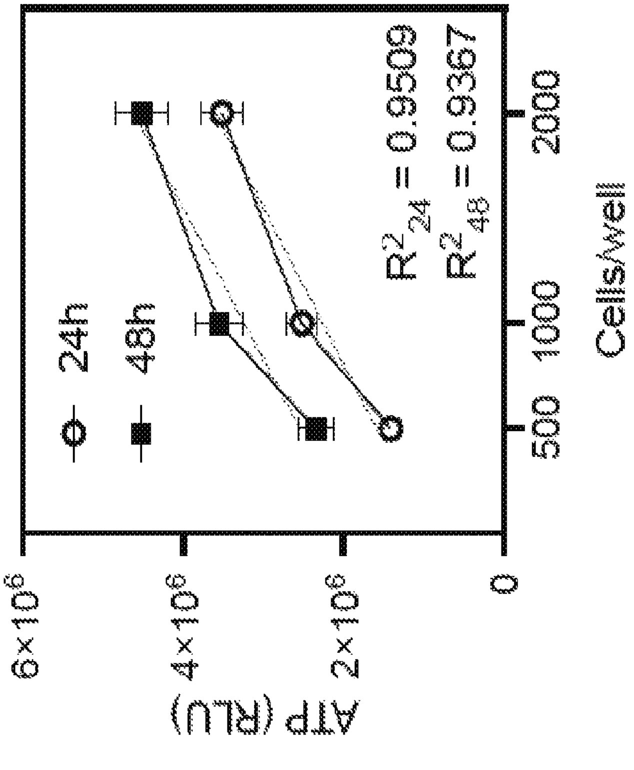
Figure 5D:
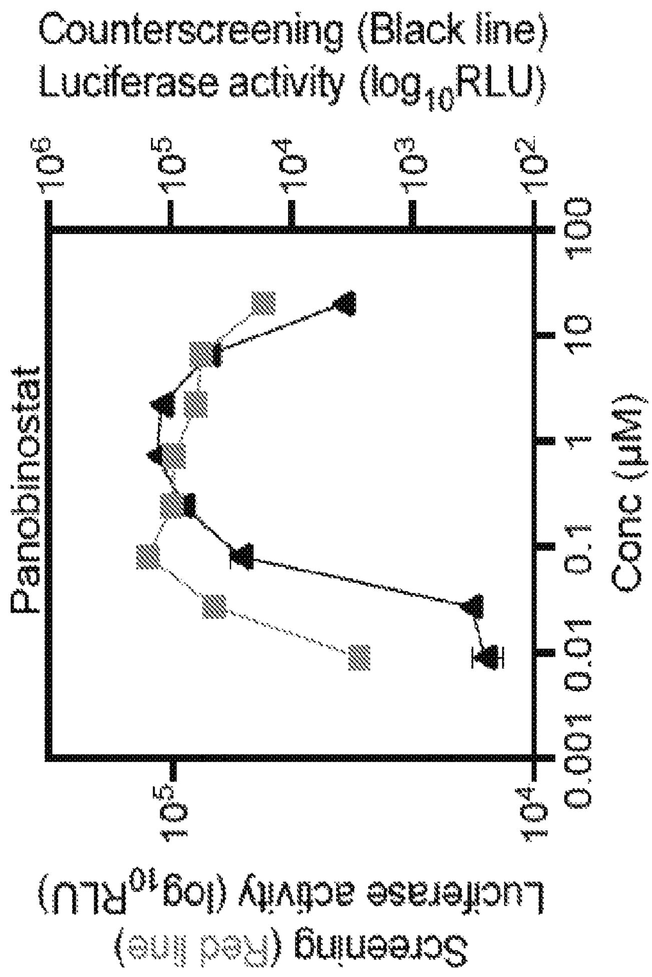

The construct for generating the screening $C_2C_{12}$ cell line carrying the 5' and 3'UTR of the human utrophin gene is described by Moorwood. C., et al., J Biomol Screen 18, 400-406 (2013), which is incorporated herein by reference in its entirety. The screening and counterscreening stable lines in early passage $C_2C_{12}$ cells were re-derived (FIG. 1A), and tested for the incorporation and functionality of the reporter transgene. Some compounds could increase light emission independently from the 5' and 3'UTR regions, i.e., by activating the CMV promoter or increasing overall mRNA synthesis. Therefore, in order to distinguish such compounds, a counterscreening cell line stably expressing only the CMV-driven luciferase gene was generated (FIG. 1A). To determine optimal conditions for the implementation in a 384-wells high-throughput format, evaluated were DMSO tolerance, optimal cell density and incubation time (FIG. 5A-5C). The screening line performed robustly at the tested concentrations of DMSO (0 to 1%), with coefficient of variation (CV) lower than 10% for both luciferase activity and cell viability (quantified as ATP content) (Table 1 and FIG. 5A). Luciferase activity (FIG. 5B) and cell viability (FIG. 5C) increased linearly as a function of cell density (500, 1000, 2000 cells/well) and incubation time (24 or 48 hours post-treatment). Based on these results, the experimental design consisted in plating 1000 cells/well, allowing them to attach for 24 h, then treating them with compounds with a 0.2% DMSO final concentration, and assaying luciferase activity after a 24 h incubation (FIG. 1B). Panobinostat (S1030) was chosen as positive control for its capacity to induce overall mRNA transcription and luciferase expression at concentrations within the nanomolar to micromolar range in both screening and counterscreening assays (FIG. 5D). While maximum luciferase activity was comparable between screening and counterscreening after treatment with Panobinostat, basal activity was approximately 80 times higher in the screening cell line (FIG. 5D).

Example 2

Screening Library

A custom generated library of small molecules enriched for FDA approved compounds (1164) and compounds with known pharmacological activity (1836) from SelleckChem was screened. The library consists of 373 known kinase inhibitors, 246 compounds classified as cancer chemotherapeutics, 150 inhibitors of epigenetic regulators, 358 GPCR and Ion Channel inhibitors, with the remaining 2000 compounds falling into diverse target classes (e.g., protease, microbiology, etc.). Compounds were suspended in DMSO, arrayed in columns 3-22 of 384 well microplates, and stored at −20° C. Library plates were thawed a maximum of 10 times to maintain compound integrity.

Results of SelleckChem Library Screening

Figure 1C:
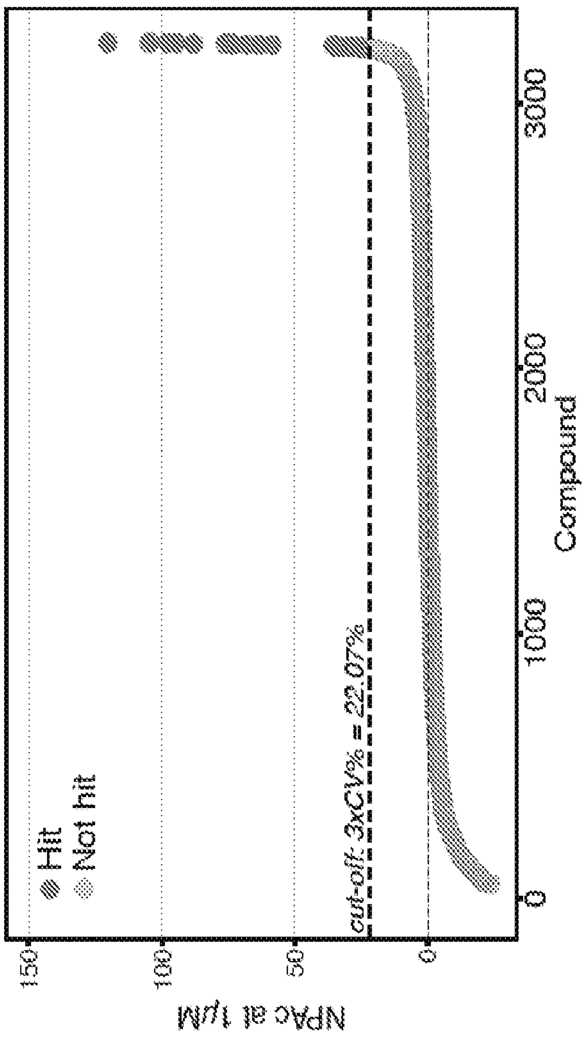
Figure 1D:
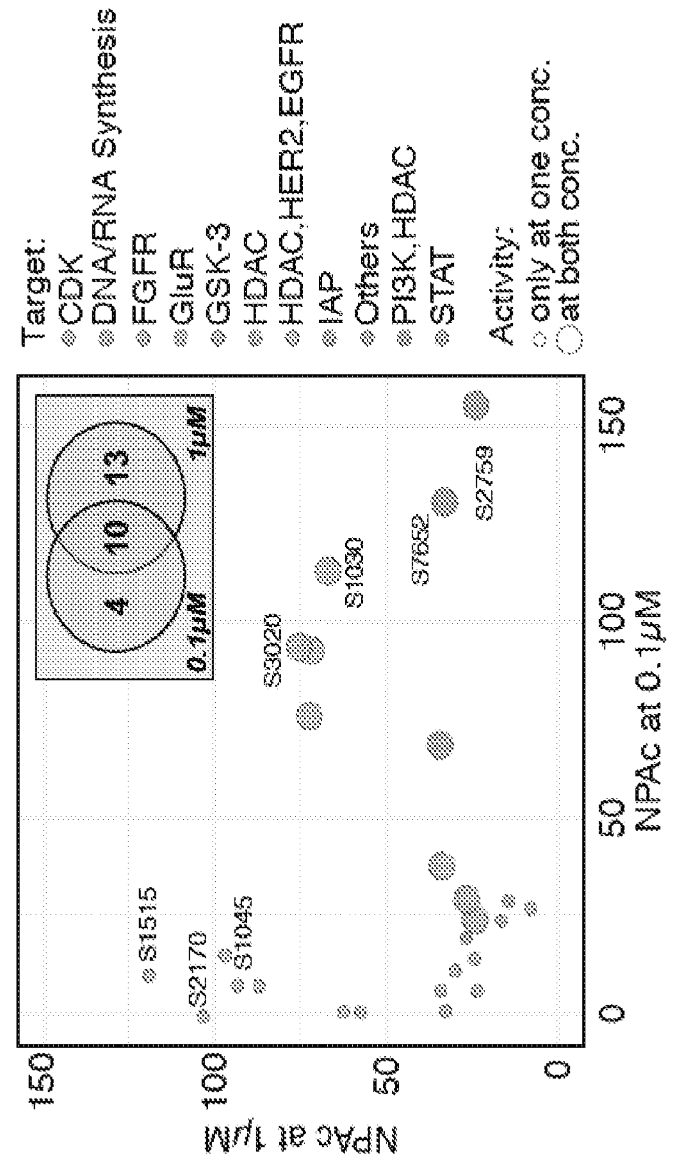
Figure 1E:
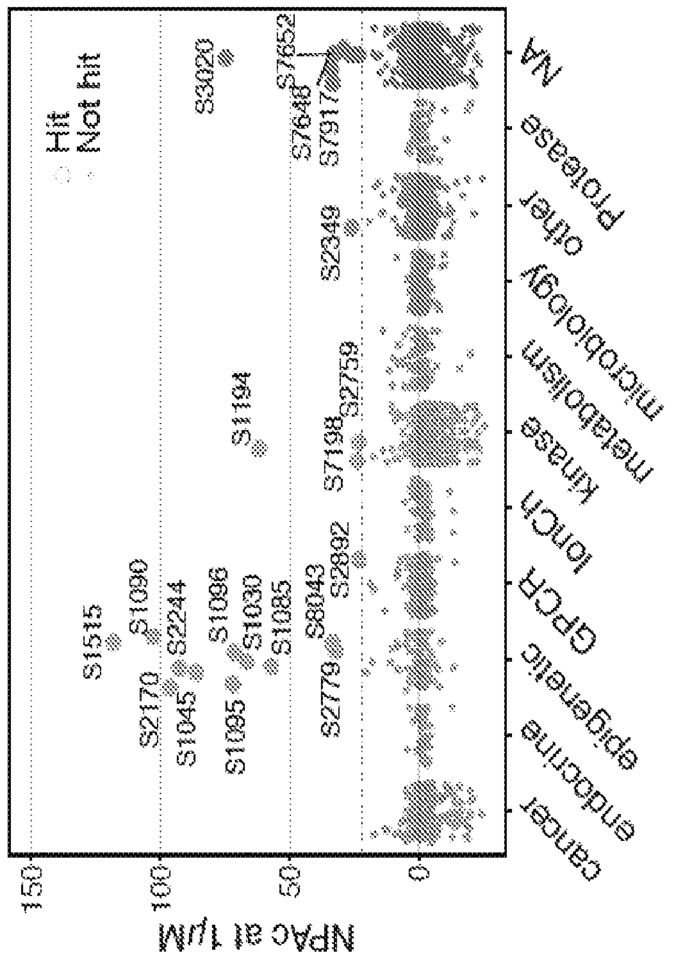
Figure 5E:
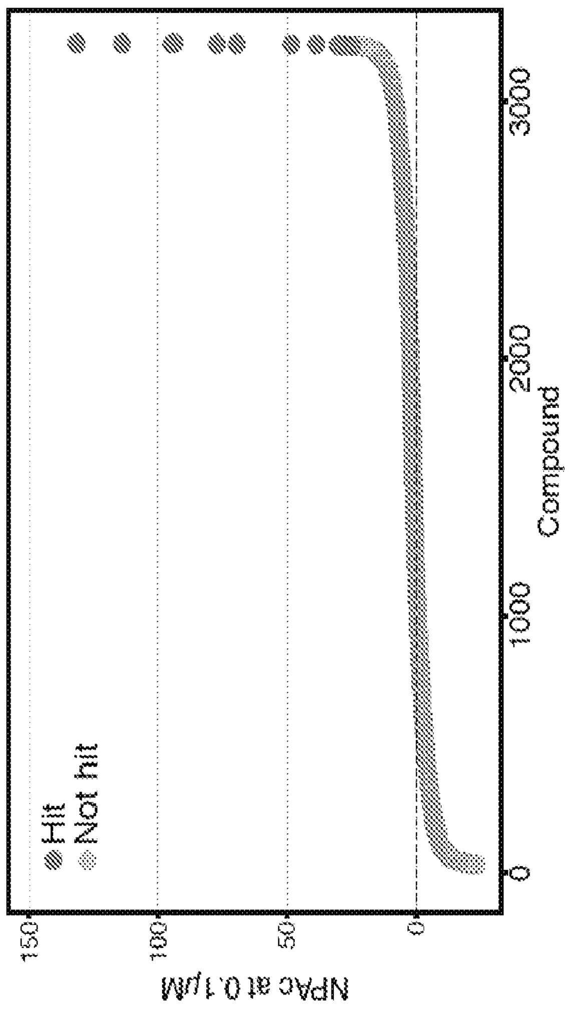
Figure 5F:
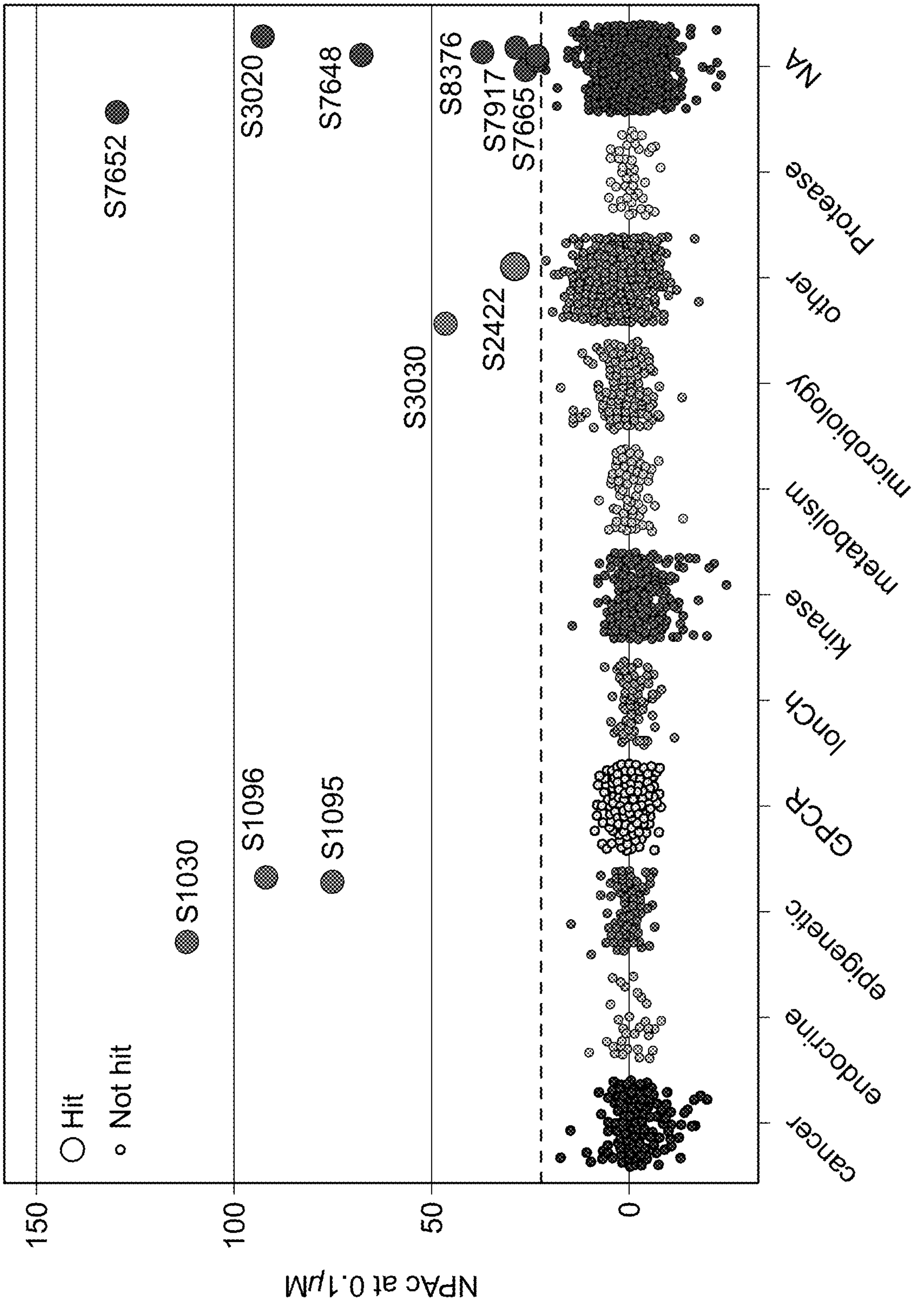

To identify small molecules capable of increasing utrophin expression, a curated Bioactive Screening Library (SelleckChem) containing 3127 compounds with known biological and pharmacological activities, including many FDA-approved drugs, was screened. The screen was performed at two concentrations, 1 μM (FIG. 1C) and 0.1 μM (FIG. 5E). By using a threshold of 22.07% activation, corresponding to 3 times the standard deviation of the average NPAc (Normalized Percent Activation), a total of 27 hits were detected that were active across the two concentrations. Of these, 4 were active only at 0.1 μM, suggesting possible cytotoxicity at higher concentrations, while 13 were active only at 1 μM (FIG. 1D). The majority of the hits are compounds targeting epigenetic regulators (i.e., HDAC) and kinases (i.e., PI3K, GSK-3) (FIG. 1E and FIG. 5F). Panobinostat (S1030) was included in the screening library and, as a validation of the approach, was detected in the assay as active at both concentrations.

Example 3

Dose-Response in Screening and Counterscreening Assays

Figure 2A:
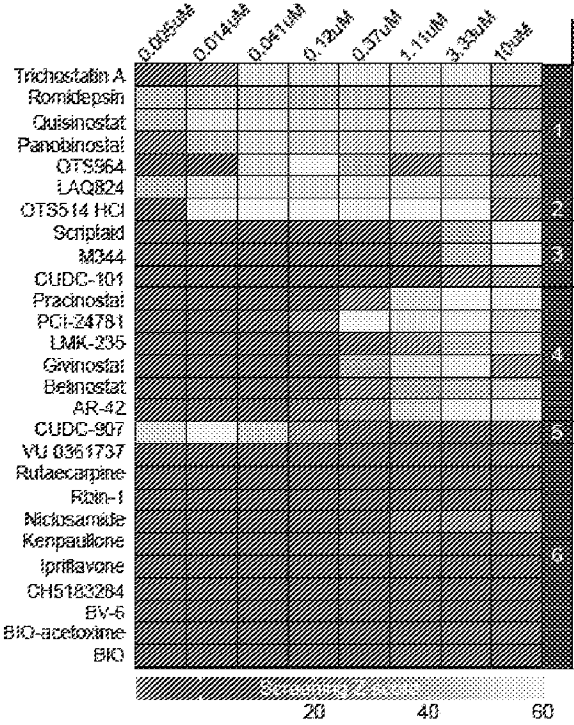
FIGS. 2A-2E show dose-response assay, H2LPS calculation and hit validation.
Figure 2B:
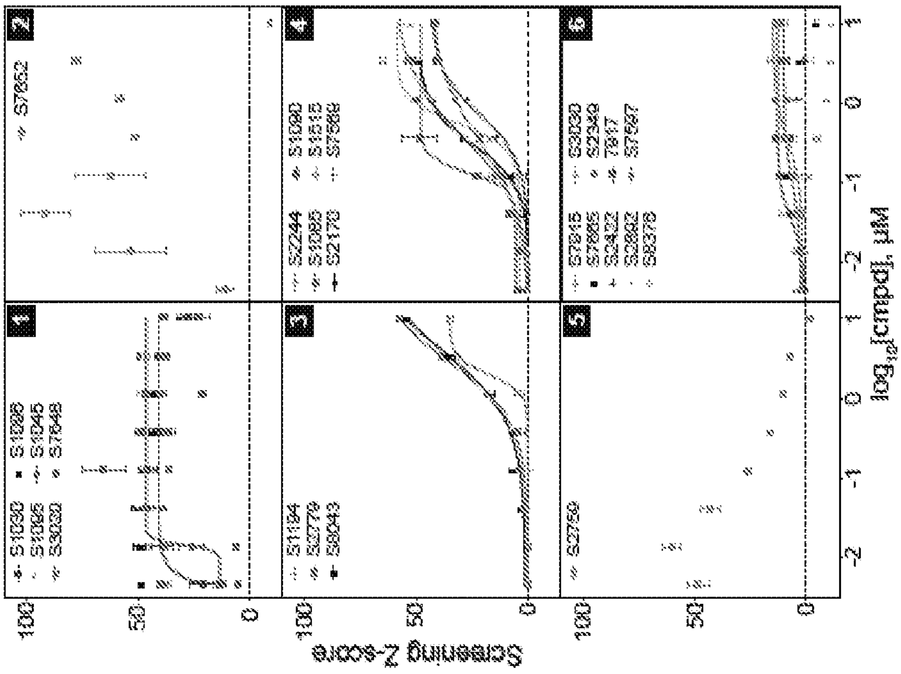
Figure 6:
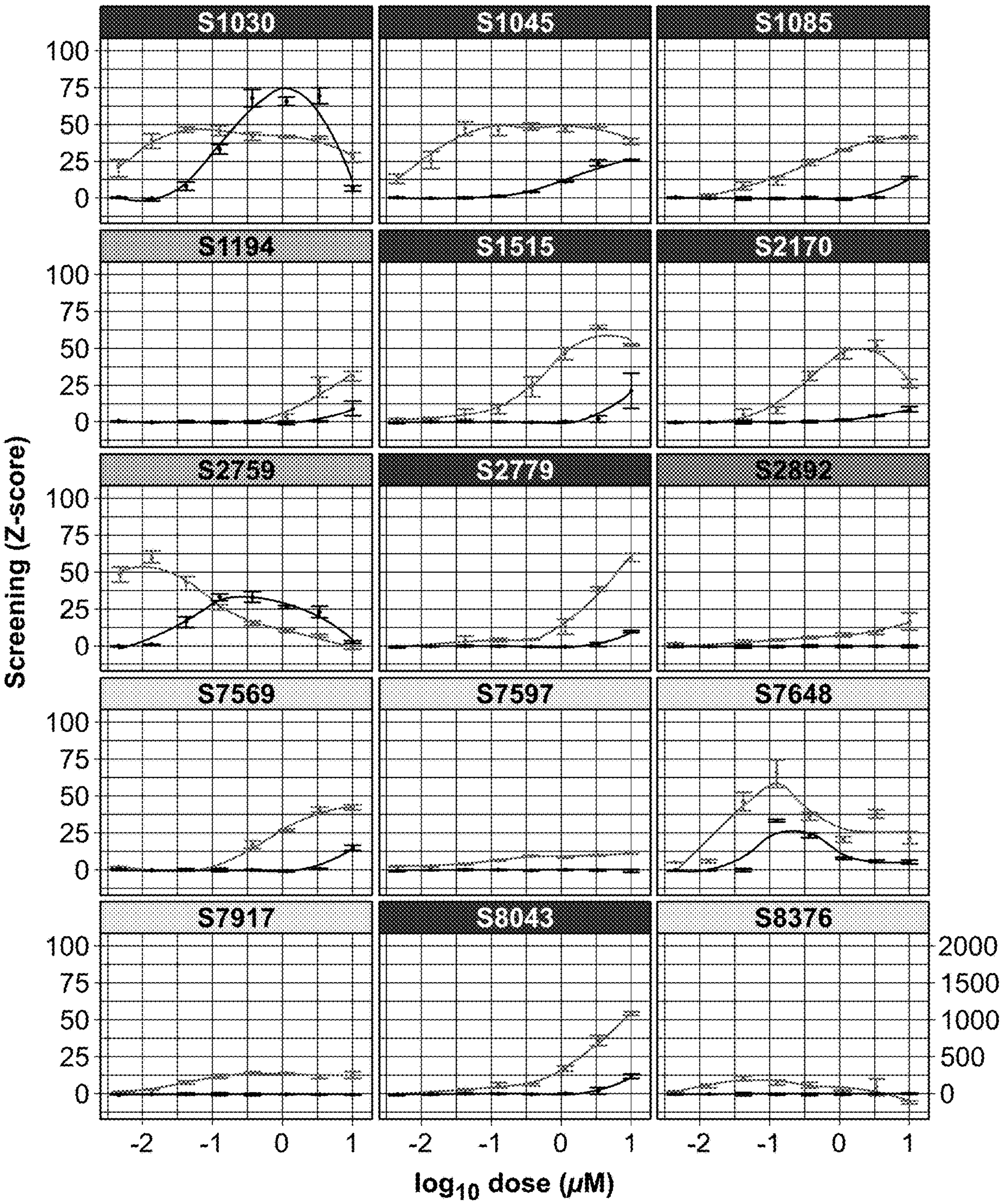
FIG. 6 shows raw dose-response traces for screening (red) and counterscreening (black) of the 27 selected hits. Values are mean and standard error of the mean [n=4 wells/compound]. Headers of different colors identify the target class (Epigentic, GPCR, Kinase or Other).
Figure 6:
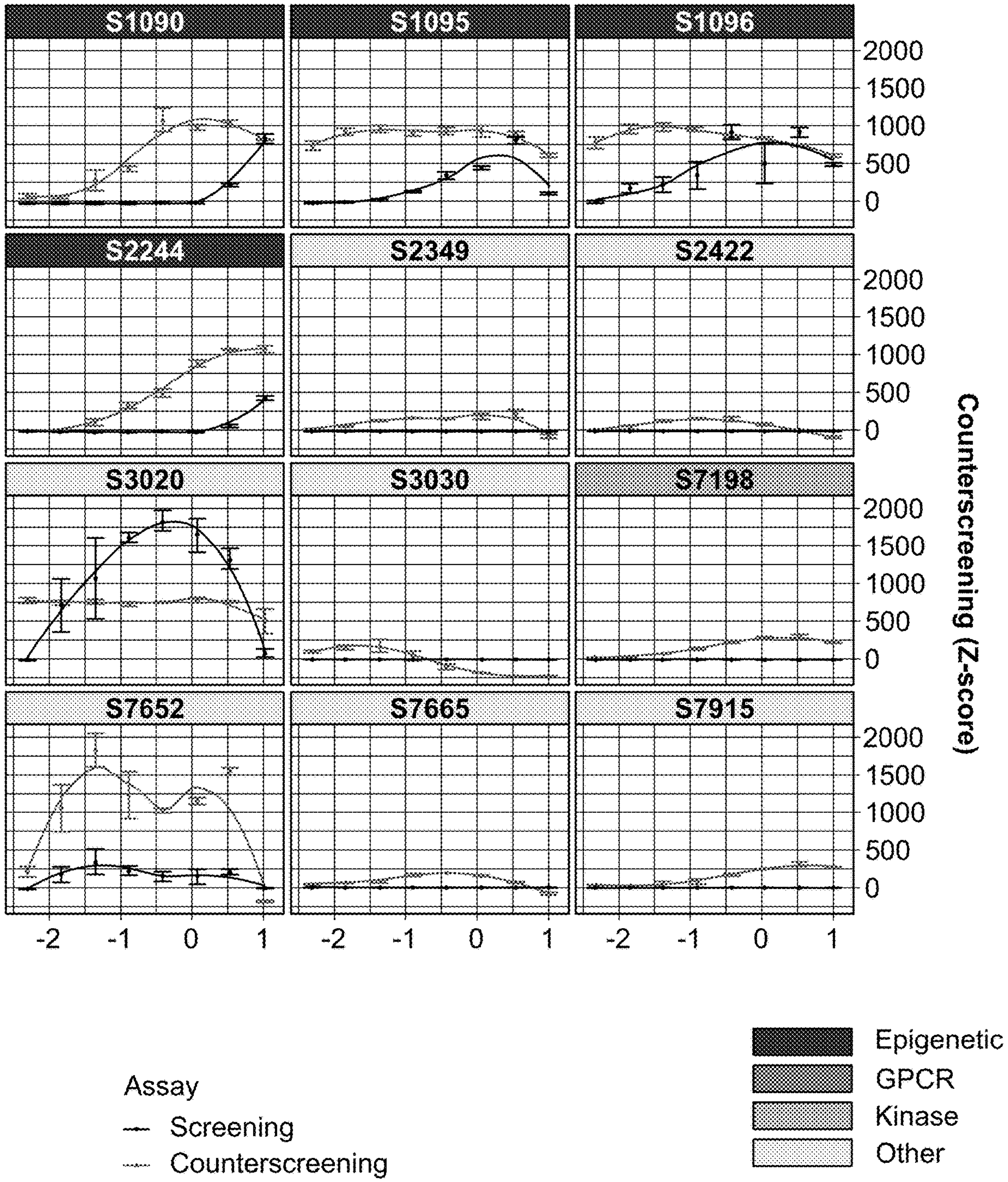

A first criterion for evaluating the performance of the selected hits was whether their activity was dose-dependent. After performing a dose-response analysis (5 nM to 10 μM) of each hit in the screening cell line, a clustering approach was applied (complete linkage with Euclidean distance measurement) to highlight similarities between compounds profiles. The algorithm grouped the 27 compounds in 6 clusters based on their dose-response profile (FIG. 2A). From this initial analysis, cluster 2, 5 and 6 included compounds with either unsatisfactory dose-response profile, very low potency and/or with potential cytotoxicity. Clusters 1, 3 and 4 included promising compounds, with high activity and low cytotoxicity. By modeling each dose-response trace with a 4-parameter logistic model applied to the Z— score values (FIG. 2B), the $EC_{50}$ of each molecule was calculated. Clusters 1 and 4 included compounds with high potency and $EC_{50}$ on the order of 10 nM and 100-700 nM respectively (FIG. 2A and panels 1 and 4 of FIG. 2B). The hits in cluster 3 gave a clear dose-dependent activation but had $EC_{50}$s in the μM range (FIG. 2A and panel 3 in FIG. 2B). The same 4-parameter logistic model was applied to determine whether compounds had unwanted dose-dependent activity in the counterscreening assay, likely due to a capacity to activate the CMV promoter in the reporter transgene or to increase overall mRNA transcription. From a comparison of screening and counterscreening traces, hits S1030, S3020, S2759 and S7648 had significant luciferase activity in the counterscreening assay (FIG. 6).

Example 4

High Throughput Screening 1000 cells were seeded in a volume of 25 μL per well of 384-well Corning 3750 microplates using a MULTI-DROP™ Combi Reagent Dispenser (Thermo Scientific). Cells were allowed to attach overnight at 37° C., 5% $CO_2$ in a humidified chamber. Drugs (50 nL) were transferred to assay plates using a 384, 50 nL slotted pin tool (V&P Scientific) and a JANUS Automated Workstation (Perkin Elmer). Compounds were added to a final concentration of 1 μM and 100 nM in 0.2% DMSO. Columns 1 and 23 were treated with 0.2% DMSO (negative control). Columns 2 and 24 were treated with 100 nM Panobinostat (positive control). Cells were incubated for 24 hours at 37° C., 5% $CO_2$. Assay plates were removed from the incubator for 1 hour to equilibrate to room temperature, prior to adding 254 of 0.5×Britelite (PerkinElmer). Luminescence was measured on an EnVisionXcite Multilabel Plate Reader (PerkinElmer), using ultrasensitive luminescence measurement technology.

Data Analysis and H2LPS Score

Raw values from DMSO and Panobinostat control wells were aggregated and used to calculate z'-factors [1-(3*($DMSO_{sd}$+$Panobinostat_{sd}$)/Abs($DMSO_{avg}$−$Panobinostat_{avg}$))] for each assay plate, as a measure of assay performance and data quality, with a z'-factor>0.5 representing acceptable data. Raw data values of sample wells were normalized to aggregate DMSO and Panobinostat plate control wells and expressed as Normalized Percent Activation [NPAc=(($DMSO_{avg}$−Test well)/($DMSO_{avg}$−$Panobinostat_{avg}$))×100] and Z-score [Z=(Test well−$DMSO_{avg}$)/($DMSO_{sd}$)]. A hit-rate cutoff of 22.07% activation was calculated as (3*Stdev[NPAc])+Avg[NPAc]. Data wrangling and visualization were performed in R version 3.5.1. Dose-response analysis was done with the dr4p1 package (version 1.1.7.5) for R, using the following parameters: trend=increasing; method.init=logistic; method.robust=Huber.

A Hit 2 Lead Prioritization Score (H2LPS) was designed and developed as a tool for ranking and prioritizing hits prior to in vitro validation and preclinical evaluation. H2LPS is a unitless parameter designed to be directly proportional to the performance of the hit on the screening assay using multiple parameters. To obtain the H2LPS, initial scores were calculated separately for $EC50_{screen}$, fold difference between the $EC_{50}$s of screening and counterscreening, and success in fitting a 4-parameters logistic dose-response curve using the dr4p1 package for R. A Curve Fitting score of 1 was given if the dose-response data from the screening could be successfully fitted using the dr4p1 package, or 0 if the fitting was not successful. The difference between upper and lower boundaries of the fitted dose-response screening curve was factored in the final HPS score calculation. The $EC50_{screen}$ score was 4 if $EC50_{screen}$<50 nM (or if no $EC_{50}$ could be calculated), 3 if $EC50_{screen}$<100 nM, 2 if $EC50_{screen}$<104 and 1 if $EC50_{screen}$>1 μM. Finally, the Fold Difference score was 2 if fold difference>10, 1 if fold difference>2 and 0 if fold difference<2. The final formula for the H2LPS therefore was H2LPS=Curve Fitting score*(upper—lower limits of fit)*$EC50_{screen}$ score*Fold Difference score.

Results of H2LPS-Based Ranking and Hit Confirmation

Figure 2C:
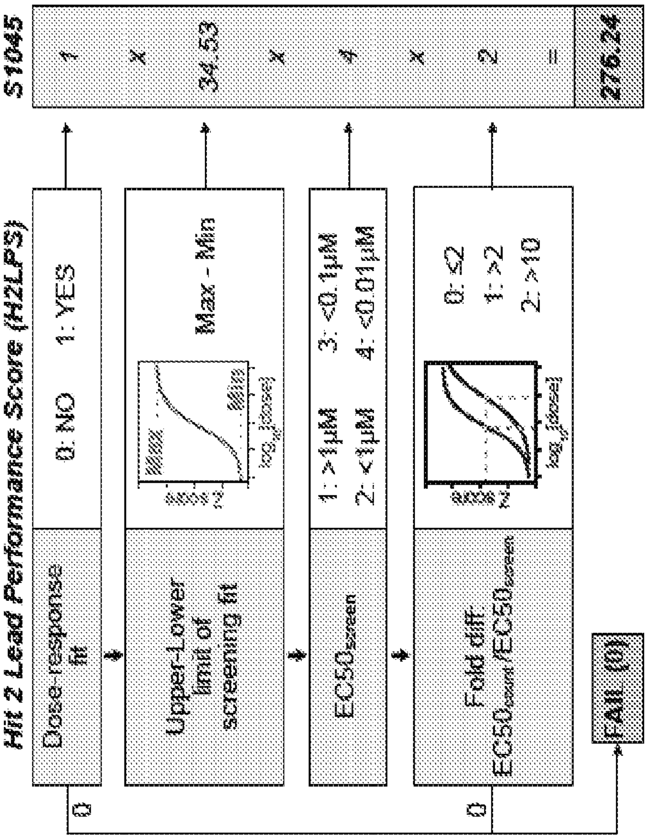

To automate the ranking and prioritizing of hits in an objective manner for further characterization, the H2LPS of individual hits was computed, which takes into account the difference between $EC_{50}$ determined in screening and counterscreening, as well as the dose-dependent behavior and amplitude of each fitted dose-response curve. Unacceptable values for one or more of these parameters (e.g., no dose-dependence, or similar $EC_{50}$ between screening and counterscreening) cause the H2LPS to be equal to 0 (FIG. 2C). The score was designed to prioritize molecules with satisfactory dose-response profile, low $EC_{50}$ and high specificity, calculated as the fold difference between the $EC_{50}$s from screening and counterscreening assays. For this screen, the H2LPS ranged from 0 to a maximum of 276.27. Using this approach, 14 of the 27 identified hits had an HPS score>0 (Table 2).

TABLE 2

Hit 2 Lead Performance Score (H2LPS).

| Rank | Cat. No. | PID | Cluster | $EC_{50}$ screen | Fold diff | Curve shape score (0/1) | Upper-lower limits scoren | $EC_{50}$ score (1 to 4) | Fold diff score (0 to 2) | H2LPS* |
|---|---|---|---|---|---|---|---|---|---|---|
| 1 | S1045 | Trichostatin A (TSA) | 1 | 0.013 | 119.82 | 1 | 34.53 | 4 | 2 | 276.27 |
| 2 | S2244 | AR-42 | 4 | 0.369 | 14.72 | 1 | 59.94 | 2 | 2 | 239.74 |

TABLE 2-continued

Hit 2 Lead Performance Score (H2LPS).

| Rank | Cat. No. | PID | Cluster | $EC_{50}$ screen | Fold diff | Curve shape score (0/1) | Up per-lower limits scoren | $EC_{50}$ score (1 to 4) | Fold diff score (0 to 2) | H2LPS* |
|---|---|---|---|---|---|---|---|---|---|---|
| 3 | S1515 | Pracinostat (SB939) | 4 | 0.558 | 59.25 | 1 | 56.37 | 2 | 2 | 225.49 |
| 4 | S2170 | Givinostat (ITF2357) | 4 | 0.269 | 18.69 | 1 | 46.59 | 2 | 2 | 186.4 |
| 5 | S1090 | PCI-24781 (Abexinostat) | 4 | 0.138 | 33.72 | 1 | 44.18 | 2 | 2 | 176.72 |
| 6 | S1085 | Belinostat (PXD101) | 4 | 0.342 | High | 1 | 43.41 | 2 | 2 | 173.65 |
| 7 | S7569 | LMK-235 | 4 | 0.683 | High | 1 | 43.40 | 2 | 2 | 173.61 |
| 8 | S8043 | Scriptaid | 3 | 2.438 | High | 1 | 62.01 | 1 | 2 | 124.01 |
| 9 | S1030 | Panobinostat (LBH589) | 1 | 0.013 | 9.21 | 1 | 22.06 | 4 | 1 | 88.24 |
| 10 | S2779 | M344 | 3 | 3.218 | 2.54 | 1 | 74.15 | 1 | 1 | 74.15 |
| 11 | S1194 | CUDC-101 | 3 | 1.991 | High | 1 | 34.34 | 1 | 2 | 68.68 |
| 12 | S7917 | Kenpaullone | 6 | 0.034 | 6.97 | 1 | 12.92 | 4 | 1 | 51.67 |
| 13 | S7597 | BV-6 | 6 | 0.099 | High | 1 | 7.00 | 3 | 2 | 42.02 |
| 14 | S7198 | BIO | 6 | 0.125 | 3.01 | 1 | 12 | 2 | 1 | 24 |
| 15 | S7648 | OTS964 | 1 | | | 0 | | 4 | 0 | 0 |
| 16 | S1095 | LAQ824 (Dacinostat) | 1 | | | 0 | | 4 | 0 | 0 |
| 17 | S1096 | Quisinostat (JNJ-26481585) | 1 | | | 0 | | 4 | 0 | 0 |
| 18 | S3020 | Romidepsin (FK228, Depsipeptide) | 1 | | | 0 | | 4 | 0 | 0 |
| 19 | S3030 | Niclosamide (Niclocide) | 6 | | | 0 | | 4 | 0 | 0 |
| 20 | S7652 | OTS514 hydrochloride | 2 | | | 0 | | 4 | 0 | 0 |
| 21 | S2349 | Rutaecarpine | 6 | | | 0 | | 4 | 0 | 0 |
| 22 | S2892 | VU 0361737 | 6 | | | 0 | | 4 | 0 | 0 |
| 23 | S2422 | ipriflavone (Osteofix) | 6 | | | 0 | | 4 | 0 | 0 |
| 24 | S2759 | CUDC-907 | 5 | | | 1 | | 4 | 0 | 0 |
| 25 | S7665 | CH5183284 (Debio-1347) | 6 | | | 0 | | 4 | 0 | 0 |
| 26 | S8376 | Rbin-1 | 6 | | | 0 | | 4 | 0 | 0 |
| 27 | S7915 | BIO-acetoxime | 6 | 0.33 | 0.65 | 1 | 13.04 | 2 | 0 | 0 |

Figure 2D:
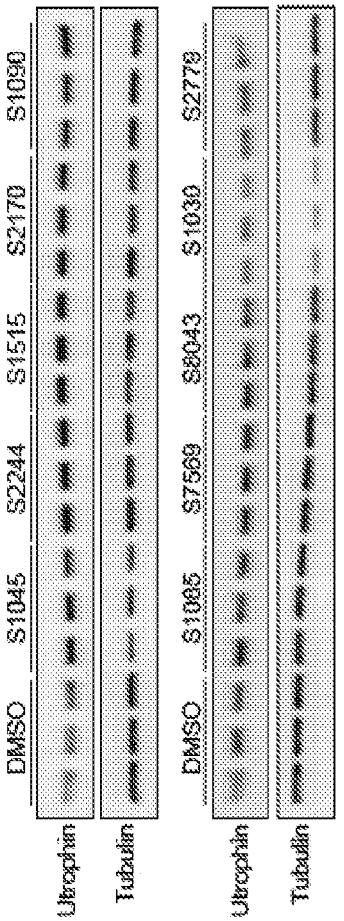
Figure 2E:
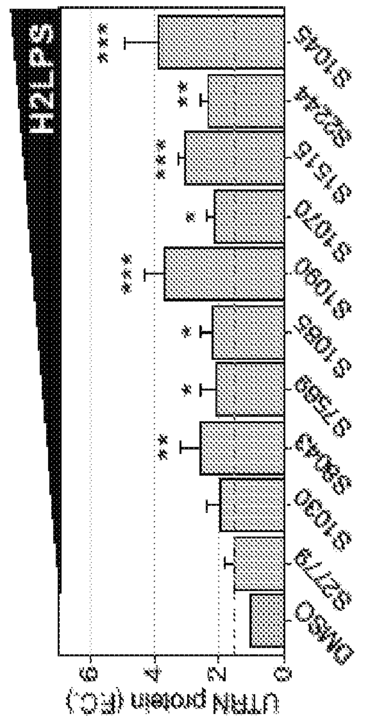

*H2LPS = Curve Shape Score
*(Upper limit-Lower Limit)
*$EC_{50}$score
*Fold Diff Score The 10 highest scoring hits were selected from this subset for performing in vitro validation. $C_2C_{12}$ cells were treated with 1 μM concentrations of the selected hits for 24 hours, followed by western blot evaluation of utrophin levels as an orthogonal assay for endogenous protein expression. Utrophin protein levels, normalized to tubulin, were significantly higher than the 0.1% DMSO control for 8 out of 10 compounds (fold increase>1.5 and P<0.05) (FIGS. 2D, 2E). Panobinostat, an FDA-approved non-selective HDAC inhibitor for cancer treatment, increased utrophin levels by 1.9-fold. One of the hits, Givinostat (S2170), a potent pan-HDAC inhibitor with demonstrated potential for treating DMD, upregulated utrophin by 2.2-fold. AR-42 (S2244), another HDAC inhibitor with proven preclinical efficacy in contrasting cancer-induced cachexia, increased utrophin by 2.3-fold and had the second highest H2LPS. Consistent with the calculated HPS, the highest scoring hit, TSA (S1045), had also the highest magnitude of protein upregulation (3.9-fold) followed by PCI-24781 (S1090; 3.7-fold). Importantly, high H2LPS was generally correlated with confirmation in WB assays (FIG. 2E).

Example 5

Preclinical Studies in Mdx Mice

Four-week-old mdx mice ($C_{57}$BL/10ScSn-DMDmdx/J) were injected intraperitoneally on alternate days with Trichostatin A (Wako Chemicals USA-Inc, Richmond, VA; dose 30 μg/kg), or an equal volume of sterile PBS for three months. All animal experiments were approved by the Institutional Animal Care and Use Committee at the University of Pennsylvania School of Medicine.

Functional in vivo and ex vivo analyses including rotarod, EDL strength, and sensitivity to damage induced by lengthening contractions (ECC), were performed as described by Krag, et al. Proc. Natl. Acad. Sci. U.S.A. 101, 13856-13860 (2004) and Bogdanovich, S. et al. Functional improvement of dystrophic muscle by myostatin blockade. Nature 420, 418-421 (2002), each of which is incorporated herein by reference in its entirety. Following the procedure, muscles were flash-frozen in liquid nitrogen-cooled isopentane and stored at −80° C.

Gene Expression and Western Blot Analyses

Total RNA was extracted from TA muscle samples with RNAeasy kit (Qiagen, USA) and reverse transcribed with random hexamers. qPCR was performed using Taqman probes for Utrophin (Assay ID Mm01168846_ml) and β-actin. Muscle tissue samples were lysed with TNEC buffer (50 mM Tris-HCl, pH 8.0; 150 mMNaCl; 1% NP40; 2 mM EDTA) buffer containing complete protease inhibitor cocktail (Roche, Basel, Switzerland). $C_2C_{12}$ cells were treated for 24 h with 1 μM concentrations of compounds from a fresh batch (3 wells for each compound), and cell samples were lysed with RIPA buffer with protease inhibitor cocktail. The experiment was repeated three independent times. 50-75 μg of total proteins from muscle tissues, or 4 μg of cell protein extracts, were resolved on a 3-8% Tris-Acetate gradient gel (NuPage; Invitrogen), transferred to PDVF or nitrocellulose membranes and mouse monoclonal anti-utrophin antibody MANCHO3 clone 8A4 (developed by Glenn E. Morris and obtained from the Developmental Studies Hybridoma Bank, Iowa) or a custom-made anti-UtrophinA rabbit polyclonal antibody (muscle tissue samples) generated and described previously by Chakkalakal et al., Nucleic Acids Res. 36, 826-838 (2008), which is incorporated herein by reference in its entirety.

Results of In Vitro Validation of the Highest Scoring Hit, TSA

Figure 3A:
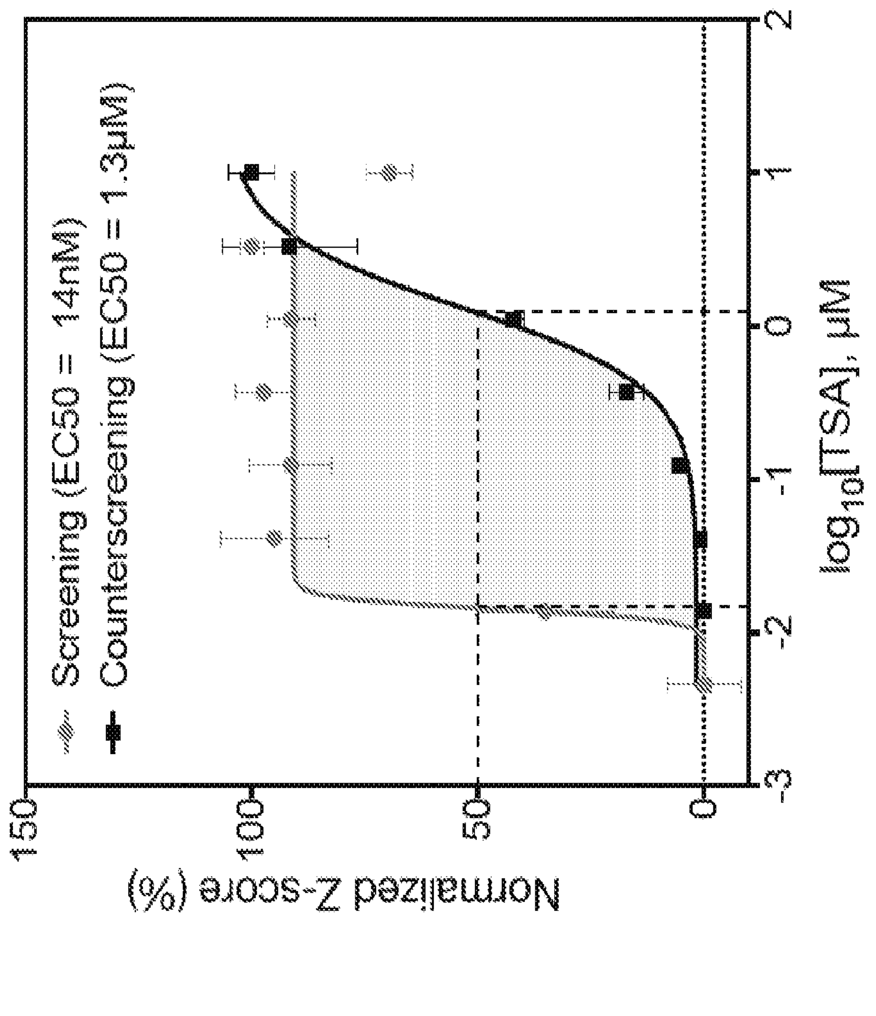
FIGS. 3A-3C show in vitro validation of the highest scoring hit (TSA—S1045).
Figure 3B:
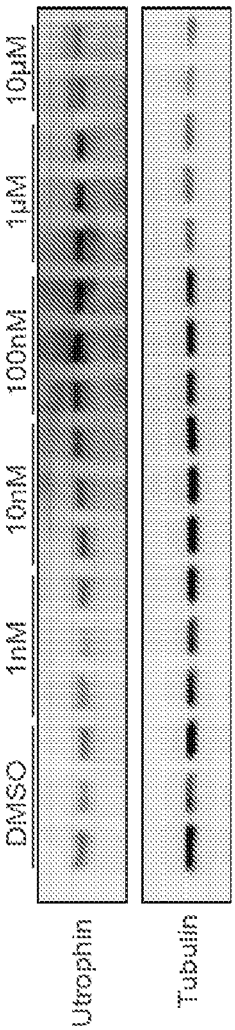
Figure 3C:
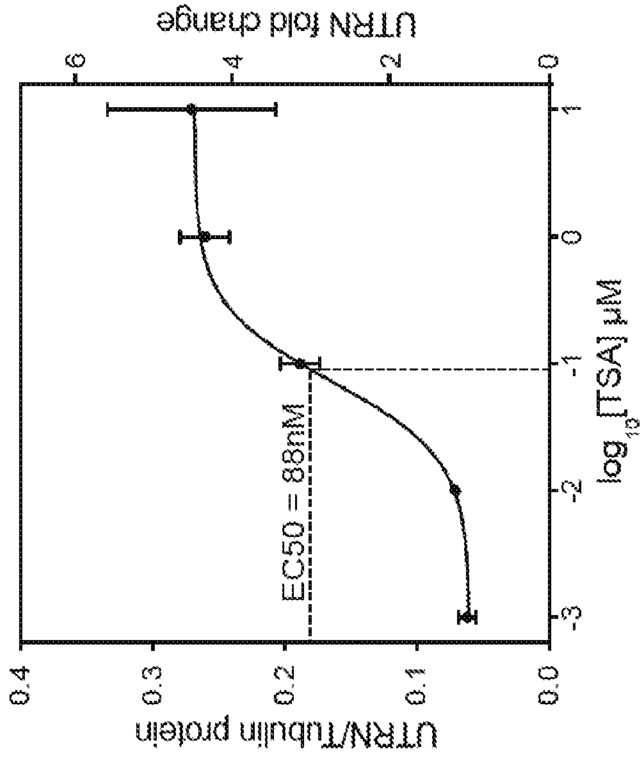

TSA is a broad-spectrum HDAC inhibitor. One of the factors contributing to its high H2LPS is the significant window between the screening $EC_{50}$ (13 nM) and counter-screening $EC_{50}$ (1.3 μM) (FIG. 3A). To further validate in vitro the dose-dependent capacity of TSA to upregulate utrophin protein, $C_2C_{12}$ cells were treated for 24 hours with increasing concentrations of TSA (from 1 nM to 10 μM) (FIG. 3B). Consistent with the single-dose western blot validation experiments, utrophin protein levels were increased 4.3 times by 1 μM TSA. The calculated $EC_{50}$) for utrophin protein levels was 88 nM (FIG. 3C). Some cytotoxicity was evident for TSA concentrations higher than 1 μM. This data suggests that, at nanomolar TSA concentrations, the interaction with the 5'3'UTRs of the utrophin significantly contributes to the increase in utrophin expression.

Results of In Vivo TSA Treatment in the Mdx Mouse Model of DMD

Figure 4A:
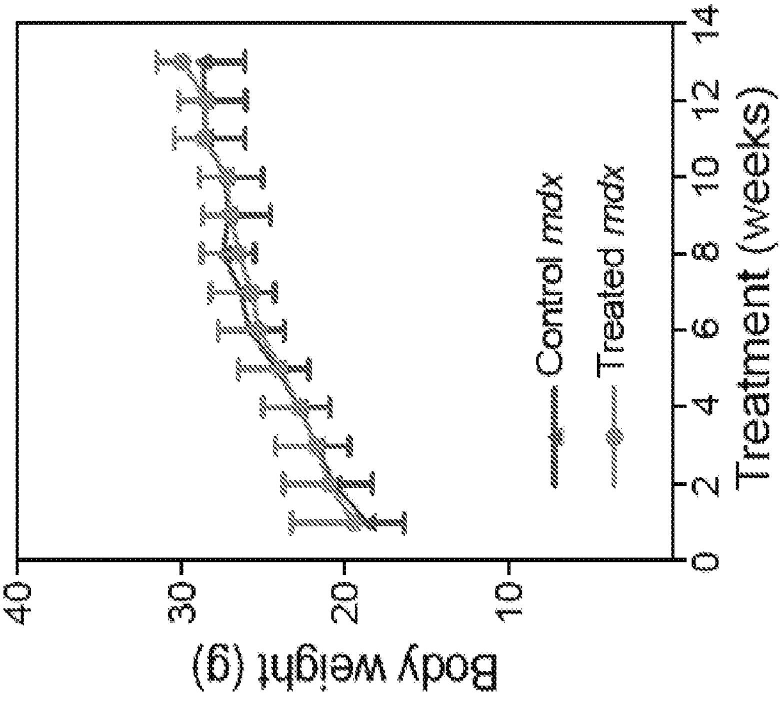
FIGS. 4A-4G show in vivo preclinical validation of TSA treatment in the mdx mouse model of DMD.

To test the ability of TSA to increase utrophin in vivo and improve the dystrophic phenotype, 4 week-old mdx mice were treated with i.p. injections of 30 μg/kg body weight TSA, on alternating days for a total of 3 months. TSA did not affect body weight (FIG. 4A) or the wet weight of skeletal muscles and organs compared to control-treated mice (Table 3).

TABLE 3

Body, muscle and organ weights of control and treated mdx mice.

| | N | Control mdx | Treated mdx | P |
|---|---|---|---|---|
| Body weight (g) | 11 (mice) | 29.2 ± 0.8 | 30.2 ± 0.5 | 0.3008 |
| Muscles (mg) | 18 (muscles) | | | |
| EDL | | 17.6 ± 0.6 | 17.5 ± 0.4 | 0.5785 |
| Soleus | | 13.2 ± 0.7 | 12.8 ± 0.4 | 0.6088 |
| Tibialis Anterior (TA) | | 68.0 ± 2.2 | 66.1 ± 1.5 | 0.4855 |
| Gastrocnemius | | 194.6 ± 6.3 | 213.0 ± 11.0 | 0.5062 |
| Quadriceps | | 239.9 ± 10.9 | 234.6 ± 8.7 | 0.7058 |
| Organs (mg) | 11 (organs) | | | |
| Heart | | 170.6 ± 10.9 | 159.7 ± 5.2 | 0.5503 |
| Liver | | 1260.0 ± 85.0 | 1179.0 ± 36.4 | 0.6063 |
| Kidneys | 8 | 544.3 ± 18.8 | 532.3 ± 25.8 | 0.7106 |

Figure 4B:
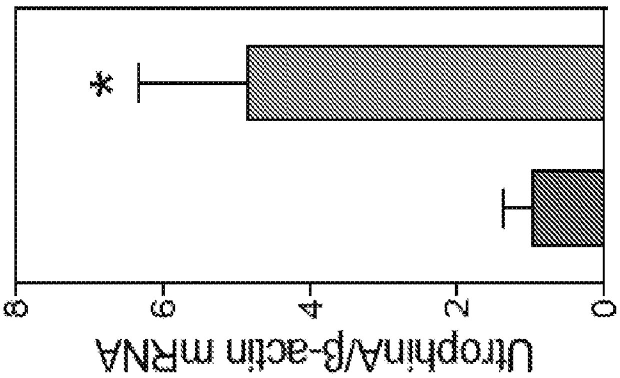
Figure 4C:
Figure 4D:
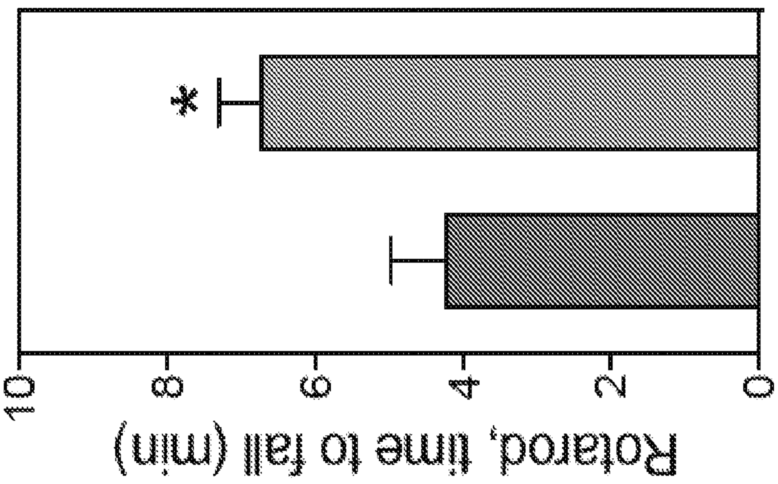
Figure 4E:
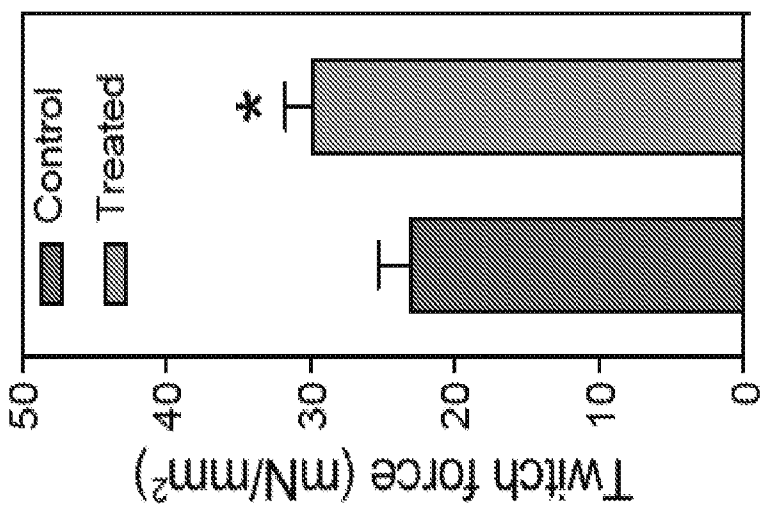
Figure 4F:
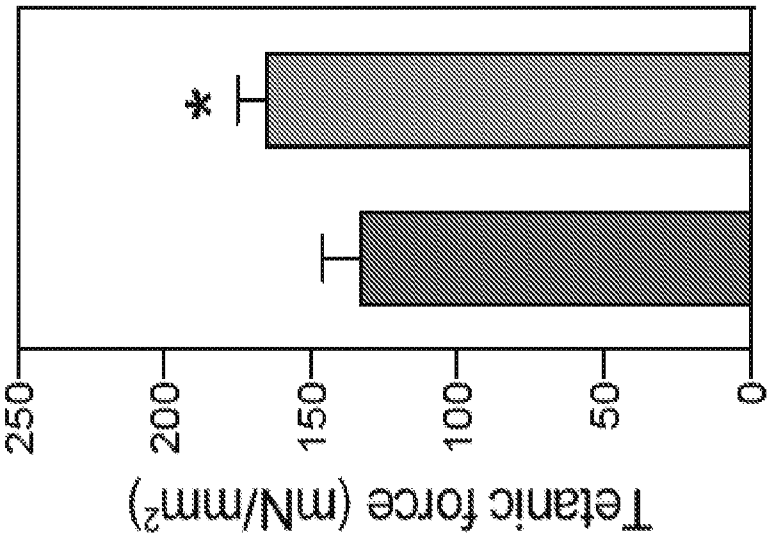

Utrophin mRNA (FIG. 4B) and protein (FIG. 4C) levels were increased by 4.9-fold and 2-fold respectively in TA muscle. The higher utrophin expression was associated with a significant increase in muscle performance both in vivo (FIG. 4D) and ex vivo (FIGS. 4E, 4F). Treated mdx mice performed significantly better than control mdx on a rotarod test, which assays motor coordination, postural control and fatigability, as described by Grounds et al., Neurobiology of Disease 31, 1-19 (2008), which is incorporated herein by reference in its entirety, (FIG. 4D). Consistently, isometric twitch and tetanic strength of EDL muscles were significantly higher in TSA treated mice, both before (Table 4) and after normalization by crossectional area (FIGS. 4E, 4F and Table 4), suggesting that TSA improved muscle contractility without increasing muscle mass.

TABLE 4

Contractile, morphometric and biochemistry measurements.

| | n | Control mdx | Treated mdx | P |
|---|---|---|---|---|
| EDL contractility | | | | |
| Twitch force (mN) | 18 | 49.91 ± 4.61 | 64.19 ± 4.22 | 0.0287* |
| Twitch force (mN/mm$^2$) | 18 | 23.19 ± 2.15 | 29.98 ± 1.84 | 0.0220* |
| Tetanic force (mN) | 18 | 284.6 ± 23.42 | 351.9 ± 16.61 | 0.0250* |
| Tetanic force (mN/mm$^2$) | 18 | 133.5 ± 12.50 | 166.0 ± 9.09 | 0.0434* |
| ECC force drop 1-5 (%) | 18 | 36.58 ± 3.09 | 25.81 ± 4.46 | 0.0114* |
| EDL morphometry | | | | |
| $L_0$ (mm) | 18 | 11.34 ± 0.20 | 12.16 ± 0.20 | 0.0068** |
| CSA (mm$^2$) | 18 | 2.18 ± 0.09 | 2.20 ± 0.13 | 0.8717 |
| CNF (%) | 18 | 34.82 ± 2.72 | 24.62 ± 2.30 | 0.007** |
| Biochemistry | | | | |
| Serum CK (U/L) | 3 vs 4 | 10492 ± 4104 | 7450 ± 2381 | 0.6286 |

TABLE 4-continued

| Contractile, morphometric and biochemistry measurements. | | | | |
|---|---|---|---|---|
| | n | Control mdx | Treated mdx | P |
| Diaphragm Hydroxyproline TA (μg/mg) | 6 | 0.92 ± 0.02 | 0.90 ± 0.06 | 0.2814 |
| Diaphragm Hydroxyproline Diaphragm (μg/mg) | 6 | 3.44 ± 0.22 | 3.33 ± 0.22 | 0.4156 |

CSA, cross sectional area; ECC, eccentric contraction; $L_0$, muscle length; CNF, centrally nucleated fibers.

Figure 4G:
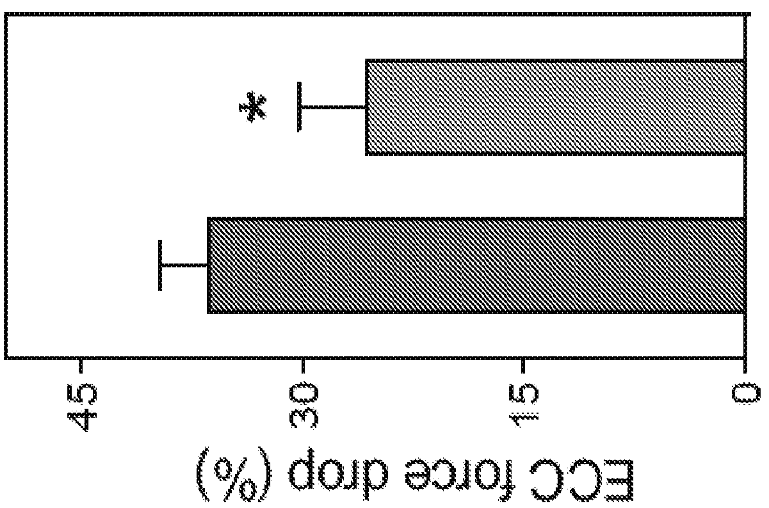
Figure 7:
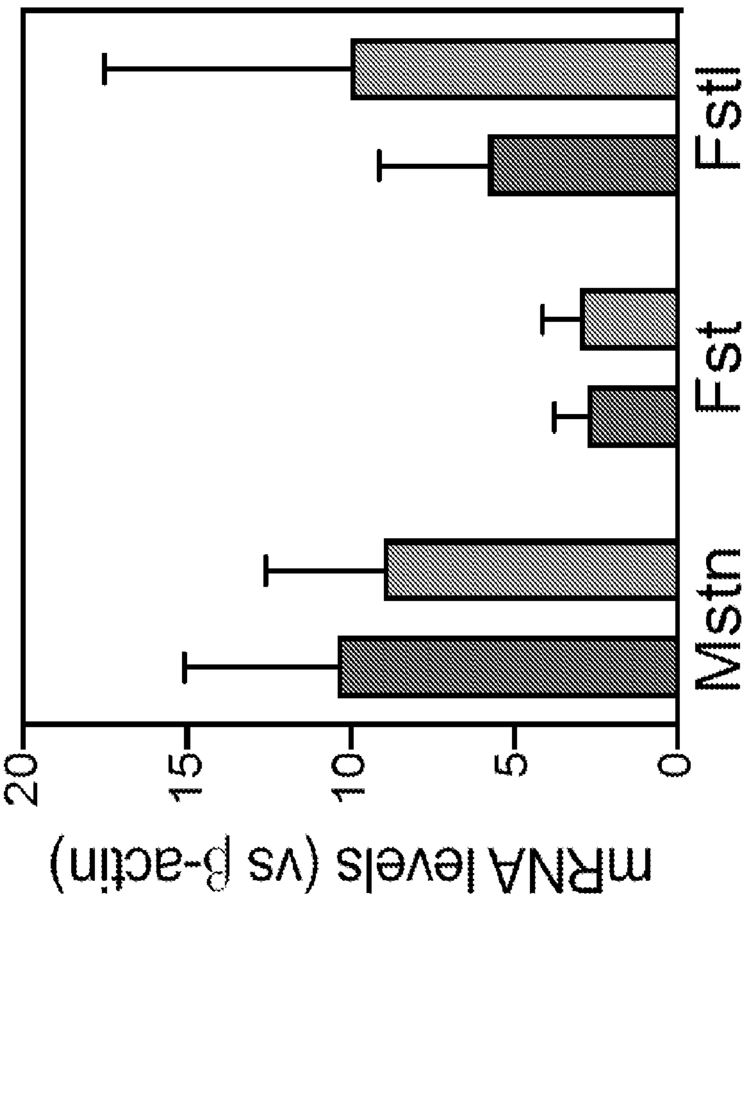
FIG. 7 shows mRNA levels of myostatin (Mstn), follistatin (Fst) and follistatin-related (Fstl1 protein in TA muscles of mdx mice following TSA treatment [n=5/group].
Figure 8:
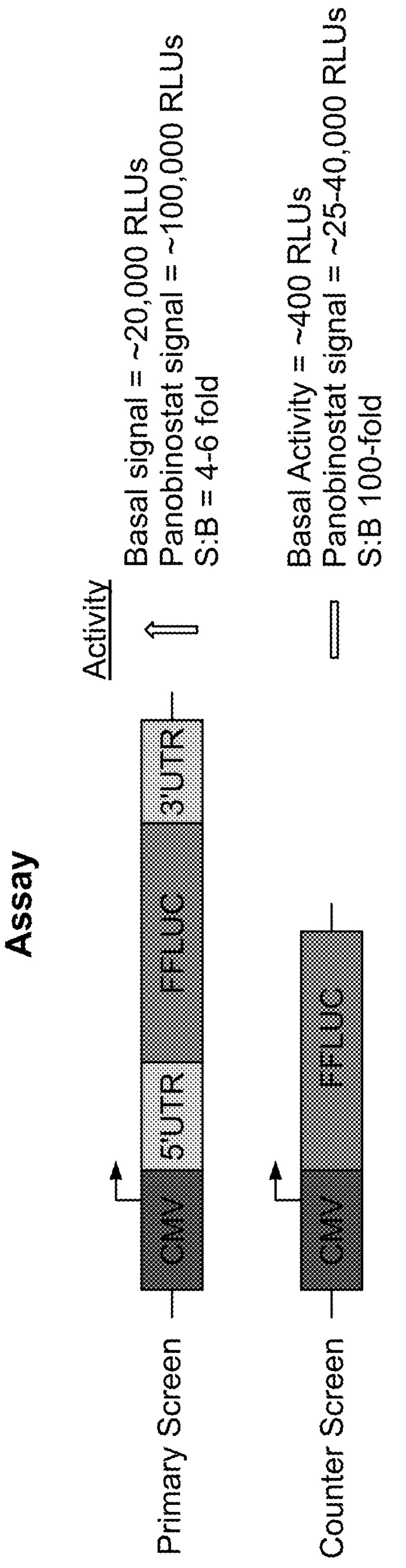
FIG. 8 shows primary screening and counterscreening constructs (similar to the respective constructs shown in FIG. 1A), with Firefly luciferase (FFLuc). The primary screening measured activity of a basal (B) signal (about 20,000 RLUs) of the stable $C_2C_{12}$-cells compared to the signal (S) (about 100,000 RLUs) of the stable $C_2C_{12}$-cells treated with Panobinostat (a pan-HDAC inhibitor, which is a positive control compound for post-transcriptional utrophin upregulation). There was a 4-6 fold increase of signal activity of the stable $C_2C_{12}$-cells treated with Panobinostat compared to the basal signal the stable $C_2C_{12}$-cells (untreated). The counterscreening measured activity of a basal (B) signal (about 400 RLUs) of the stable $C_2C_{12}$-cells (untreated) compared to the signal (S) (about 25-40,000

In addition, at the dosage used, TSA treatment did not cause changes in myostatin or follistatin gene expression (FIG. 7). No significant changes were noted in serum creatine kinase or hydroxyproline content in TA and diaphragm muscles (Table 4). A key parameter to evaluate when testing DMD treatments is susceptibility of muscle to damage caused by repeated eccentric muscle contractions (ECC), as described by Grounds et al., Neurobiology of Disease 31, 1-19 (2008); Moens et al., *J. Muscle Res. Cell. Motil.* 14, 446-451 (1993); and Petrof et al., *Proc. Natl.* Acad. Sci. U.S.A. 90, 3710-3714 (1993), each of which is incorporated herein by reference in its entirety. By applying a series of 5 ECCs, TSA treatment was found to mdx muscles from eccentric damage, as they lost on average 37% less force than control-treated muscles after the $5^{th}$ ECC (FIG. 4G). These improvements of both in vivo and ex vivo parameters were accompanied by a 30% lower number of centrally nucleated fibers (Table 4) in TSA-treated EDL muscles. Together, these data suggest that TSA treatment significantly improved the dystrophic phenotype in the mdx mouse model of DMD.

Statistical Analysis

Values are presented herein as mean±standard error of the mean. Data visualization and statistical analysis for the in vivo studies was performed using GraphPad Prism8. Comparisons between two groups were done using a two-tailed Student t-test or Mann-Whitney non-parametric test. For the western blot validation experiments, in order to account for the variability between experiments and between gels, data were analyzed in R using a linear mixed model. All statistical tests were considered significant at a $\alpha<0.05$ unless stated otherwise.

In the above described Example, an HTS was performed to identifying post-transcriptional up-regulators of utrophin expression. For this study, a previously described assay was scaled to a 384-well format; however, the technical parameters of the assay (Table 1 and FIGS. 5A-5C) suggest that the assay is amenable to scaling up to higher throughput formats (e.g., a 1536-well format) that would allow additional, more diverse libraries to be screened. Since the goal for this HTS was to validate the proposed strategy and identify small molecules capable of increasing utrophin expression with a view to DMD therapeutics, a curated library of 3127 small molecules, enriched for FDA approved drugs and compounds with known pharmacological activity (FIG. 1) was screened. The initial screen identified 27 hits (FIG. 2). By performing dose-response analyses in screening and counterscreening, and prioritizing the hits using the H2LPS algorithm (FIG. 2C), a subset of 14 compounds were identified that are highly likely to increase utrophin by targeting the mechanisms of post-transcriptional repression. A significant advantage of ranking hits with the H2LPS is that it can be computed automatically, ensuring objective evaluation and applicability to larger screening libraries. Using this approach, 13 molecules with H2LPS=0 were excluded due to poor dose-response or significant activity in the counterscreen and validated the 10 highest scoring molecules. Consistent with the high H2LPS, 8 out of 10 molecules significantly increased utrophin protein more than 1.5 times in $C_2C_{12}$ cells (FIGS. 2D, 2E). In a separate assay, hits with score equal to 0 (e.g. S7652, S1095, S1096 and 53020) failed to increase utrophin protein levels (data not shown), supporting the predictive value of the H2LPS as an efficient algorithm to optimize the progression of hits to leads for drug development.

The development of pharmacological strategies to upregulate utrophin offers a number of translational advantages over conventional approaches for dystrophin-replacement using gene therapy or stem cells. Since utrophin expression is unabated in DMD patients, the small molecule approach described here to upregulate utrophin should circumvent many of the hurdles associated with delivery, toxicity and immune reaction of conventional DMD gene therapy (e.g., immune reactions against dystrophin itself or the capsid components of the viral vectors used for gene therapy). In addition, while the cloning capacity of currently available viral vectors requires using smaller, internally truncated forms of dystrophin or utrophin, the approach described herein allows targeting the natural, full length version. Using small molecules also offers advantages in terms of delivery, stability and bioavailability, especially for drugs that already exist in the pharmacopeia (e.g., repurposing), which already have been optimized for absorption, distribution, metabolism and excretion and toxicity (ADMET) properties in humans and are a prime focus of ongoing research.

The screening described herein independently highlights the potential of two molecules (Givinostat and TSA) that have been suggested for DMD therapy. Givinostat (S2170) was recently shown to improve DMD pathophysiology by reducing inflammatory infiltration and fibrosis, and promoting muscle regeneration in mdx mice and in boys with Duchenne and is currently in Phase III trials in humans. TSA (S1045), has been shown to have pro-myogenic effects in $C_2C_{12}$ cells, protect against unloading-induced muscle atrophy, increase tetanic force in dystrophic myotubes and muscles. Previous studies have shown that TSA can directly activate the utrophin promoter as well as increase follistatin-mediated muscle regeneration. Herein it is demonstrated that TSA can also increase utrophin levels post-transcriptionally by interacting with the 5'3'UTR in the utrophin mRNA. In the assays described herein, the $EC_{50}$ for TSA was 100 times lower when the reporter transgene carries the 5'3'UTR (screening assay) compared to when only the CMV promoter was present (counterscreening assay). The mechanism(s) of action by which TSA increases utrophin expression are likely multiple and dose-dependent, acting on utrophin promoter and UTRs. A number of hits (Givinostat, TSA and AR-42) are known HDAC inhibitors and hence are likely to demonstrate broad ranging effects on cellular and in vivo assays. Future studies will focus on separating the HDAC activity from the utrophin promoting activity to increase specificity and efficacy. Indeed, TSA is commonly used to inhibit HDAC activity and proliferation of cancer cells, with $IC_{50}$ in vitro in the nM to μM range, depending on the particular cell line. In vivo, doses up to 5 mg/kg or 10 mg/kg have been used to exert anti-tumor activity and prevent motor neuron death in a model of spinal muscular atrophy, respectively. In the study described herein, mdx mice were treated with 30 mg/kg TSA (~1 μM for a 20 g mouse) on alternating days for 14 weeks (FIG. 4). Using this paradigm, utrophin upregulation was independent of changes in myostatin or follistatin (FIG. 7). The dosage used in this study is lower than what is generally used in vivo to inhibit HDAC activity and tumor progression. Therefore, higher dosages or treatment frequency, or combinatorial drug strategies, may enhance the benefits.

In conclusion, an HTS-based strategy was used to identify and validate utrophin post-transcriptional up-regulators. As a validation of the approach, preclinical testing of the top scoring lead molecule (TSA) confirmed that it significantly improves muscle structure and function in the mdx mouse model of DMD. The hits identified herein may be complementary to those acting on the utrophin promoter as well as other strategies such as gene therapy or exon skipping. Such combinatorial approaches may help potentiate the benefits of these molecules for DMD therapy. Taken together, it is believed that the screening and counterscreening strategy described herein and H2LPS ranking will significantly facilitate future screenings of larger libraries as well.

What is claimed is:

1. A method for increasing expression of utrophin in a subject in need thereof, the method comprising administering to the subject a pharmaceutical composition comprising a post-transcriptionally utrophin upregulator compound, wherein the post-transcriptionally utrophin upregulator compound is a compound having a chemical structure of:

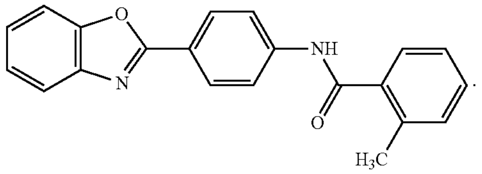 [SMILES: Cc1ccccc1C(=O)Nc1ccc(-c2nc3ccccc3o2)cc1]

2. The method of claim 1, wherein the subject has a muscular dystrophy.

3. The method of claim 2, wherein the muscular dystrophy is Duchenne Muscular Dystrophy (DMD) or Becker muscular dystrophy (BMD).

4. A method for improving a dystrophic phenotype in a muscle of a subject having loss or reduction of dystrophin protein expression, the method comprising administering to the subject a pharmaceutical composition comprising a post-transcriptionally utrophin upregulator compound, wherein the post-transcriptionally utrophin upregulator compound is a compound having a chemical structure of:

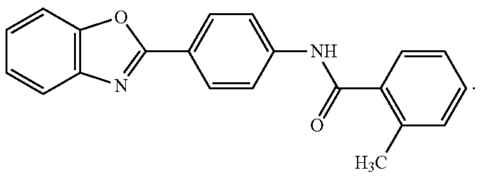 [SMILES: Cc1ccccc1C(=O)Nc1ccc(-c2nc3ccccc3o2)cc1]

5. The method of claim 4, wherein the loss or reduction of dystrophin protein expression is caused by a dystrophin gene mutation.

6. The method of claim 4, wherein the improved dystrophic phenotype is muscle function and/or performance.

7. The method of claim 6, wherein the muscle function and/or performance is motor coordination, postural control, muscle fatigability, muscle contractility and tetanic strength.

8. The method of claim 4, wherein the improved dystrophic phenotype is a muscle structure.

9. The method of claim 8, wherein the muscle structure is lower number of centrally nucleated fibers and/or an increased muscle mass.

10. The method of claim 4, wherein the improved dystrophic phenotype is a decreased susceptibility of muscle to damage caused by repeated eccentric muscle contractions (ECC) or decreased muscle wasting.

11. The method of claim 10, wherein the decreased muscle wasting is necrosis and/or atrophy.

12. The method of claim 4, wherein the subject has a muscular dystrophy.

13. The method of claim 12, wherein the muscular dystrophy is DMD or BMD.

14. A method for treating and preventing muscle wasting caused by a lack or reduced expression of dystrophin protein in a subject, the method comprising administering to the subject a pharmaceutical composition comprising a post-transcriptionally utrophin upregulator compound, wherein the post-transcriptionally utrophin upregulator compound is a compound having a chemical structure of:

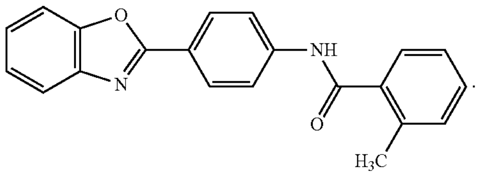 [SMILES: Cc1ccccc1C(=O)Nc1ccc(-c2nc3ccccc3o2)cc1]

15. The method of claim 14, wherein the lack or reduced expression of dystrophin protein is caused by a dystrophin gene mutation.

16. A method for treating a subject having a muscular dystrophy, the method comprising administering to the subject a pharmaceutical composition comprising a post-transcriptionally utrophin upregulator compound, wherein the post-transcriptionally utrophin upregulator compound is a compound having a chemical structure of:

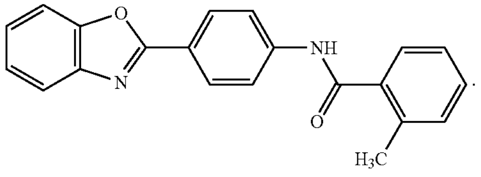 [SMILES: Cc1ccccc1C(=O)Nc1ccc(-c2nc3ccccc3o2)cc1]

17. The method of claim 16, wherein the muscular dystrophy is caused by a dystrophin gene mutation.

18. The method of claim 16, wherein the muscular dystrophy is DMD or BMD.

* * * * *